(12) United States Patent
Campbell

(10) Patent No.: US 8,562,630 B2
(45) Date of Patent: Oct. 22, 2013

(54) SUTURE INSTRUMENT AND METHOD

(75) Inventor: Richard A. Campbell, Huntsville, AL (US)

(73) Assignees: Richard Campbell, Traverse City, MI (US); Rizk El-Galley, Birmingham, AL (US)

( * ) Notice: Subject to any disclaimer, the term of this patent is extended or adjusted under 35 U.S.C. 154(b) by 1130 days.

(21) Appl. No.: 12/505,064

(22) Filed: Jul. 17, 2009

(65) Prior Publication Data

US 2010/0016870 A1    Jan. 21, 2010

Related U.S. Application Data

(60) Provisional application No. 61/129,781, filed on Jul. 18, 2008.

(51) Int. Cl.
*A61B 17/04* (2006.01)
*A61B 17/10* (2006.01)
*A61B 17/06* (2006.01)

(52) U.S. Cl.
USPC .............................. 606/144; 606/139; 606/148

(58) Field of Classification Search
USPC .......... 606/139, 144, 145, 146, 148, 103, 232
See application file for complete search history.

(56) References Cited

U.S. PATENT DOCUMENTS

| | | | | | |
|---|---|---|---|---|---|
| 5,320,632 | A | * | 6/1994 | Heidmueller | 606/144 |
| 5,507,755 | A | * | 4/1996 | Gresl et al. | 606/139 |
| 5,779,719 | A | * | 7/1998 | Klein et al. | 606/144 |
| 5,836,955 | A | * | 11/1998 | Buelna et al. | 606/148 |
| 5,860,990 | A | * | 1/1999 | Nobles et al. | 606/144 |
| 5,860,991 | A | * | 1/1999 | Klein et al. | 606/144 |
| 5,868,762 | A | * | 2/1999 | Cragg et al. | 606/144 |
| 5,954,732 | A | * | 9/1999 | Hart et al. | 606/144 |
| 6,059,800 | A | * | 5/2000 | Hart et al. | 606/144 |
| 6,117,144 | A | * | 9/2000 | Nobles et al. | 606/144 |
| 6,136,010 | A | * | 10/2000 | Modesitt et al. | 606/144 |
| 6,551,331 | B2 | * | 4/2003 | Nobles et al. | 606/144 |
| 6,562,052 | B2 | * | 5/2003 | Nobles et al. | 606/144 |
| 7,004,952 | B2 | * | 2/2006 | Nobles et al. | 606/144 |
| 7,090,686 | B2 | * | 8/2006 | Nobles et al. | 606/144 |
| 7,449,024 | B2 | | 11/2008 | Stafford | |
| 7,803,167 | B2 | * | 9/2010 | Nobles et al. | 606/144 |
| 8,197,510 | B2 | * | 6/2012 | Nobles | 606/232 |
| 2001/0031973 | A1 | | 10/2001 | Nobles et al. | |
| 2002/0045908 | A1 | * | 4/2002 | Nobles et al. | 606/144 |
| 2002/0049453 | A1 | * | 4/2002 | Nobles et al. | 606/139 |

(Continued)

*Primary Examiner* — Darwin Erezo
*Assistant Examiner* — Jing Ou
(74) *Attorney, Agent, or Firm* — B. Aaron Schulman, Esq.; Jeffrey A. Haeberlin, Esq.; Stites & Harbison PLLC

(57) ABSTRACT

A method for inserting a stitch through tissue around a hole in an abdominal muscle or a hollow organ includes: inserting into the hole a body assembly having penetration members that move from an in-line position to a deployed position, and a suture cartridge assembly secured to a forward end of the body assembly, the suture cartridge assembly having opposing arm members that move from an in-line position to a deployed position and each holding a capture sleeve to which an end of a suture cord is secured; simultaneously deploying the penetration members through the tissue around the hole and into the arm members such that the penetration members capture the capture sleeves; and simultaneously retracting the penetration members and the arm members such that the ends of the suture are retracted with the penetration members through the tissue around the hole and into the body assembly.

4 Claims, 17 Drawing Sheets

(56) References Cited

U.S. PATENT DOCUMENTS

| | | |
|---|---|---|
| 2003/0181924 A1* | 9/2003 | Yamamoto et al. ............ 606/144 |
| 2004/0006352 A1* | 1/2004 | Nobles et al. ................. 606/144 |
| 2004/0068273 A1* | 4/2004 | Fariss et al. ................... 606/144 |
| 2004/0092966 A1* | 5/2004 | Nobles et al. ................. 606/144 |
| 2004/0097978 A1* | 5/2004 | Modesitt et al. .............. 606/148 |
| 2005/0059982 A1* | 3/2005 | Zung et al. .................... 606/144 |
| 2005/0149066 A1* | 7/2005 | Stafford ........................ 606/144 |
| 2005/0228407 A1 | 10/2005 | Nobles et al. |
| 2006/0030868 A1* | 2/2006 | Bennett, III .................. 606/148 |
| 2006/0069397 A1 | 3/2006 | Nobles et al. |
| 2006/0195120 A1* | 8/2006 | Nobles et al. ................. 606/144 |
| 2007/0043385 A1* | 2/2007 | Nobles et al. ................. 606/144 |
| 2007/0167959 A1* | 7/2007 | Modesitt et al. .............. 606/144 |
| 2007/0270637 A1* | 11/2007 | Takemoto et al. ............ 600/104 |
| 2007/0276410 A1* | 11/2007 | McIntosh ...................... 606/139 |
| 2007/0276413 A1* | 11/2007 | Nobles .......................... 606/144 |
| 2007/0276414 A1* | 11/2007 | Nobles .......................... 606/148 |
| 2007/0282354 A1 | 12/2007 | McIntosh et al. |
| 2008/0269786 A1* | 10/2008 | Nobles et al. ................. 606/145 |
| 2009/0036906 A1* | 2/2009 | Stafford ........................ 606/144 |
| 2009/0048615 A1* | 2/2009 | McIntosh ...................... 606/144 |
| 2009/0088779 A1* | 4/2009 | Zung et al. .................... 606/144 |
| 2009/0112234 A1* | 4/2009 | Crainich et al. .............. 606/144 |

* cited by examiner

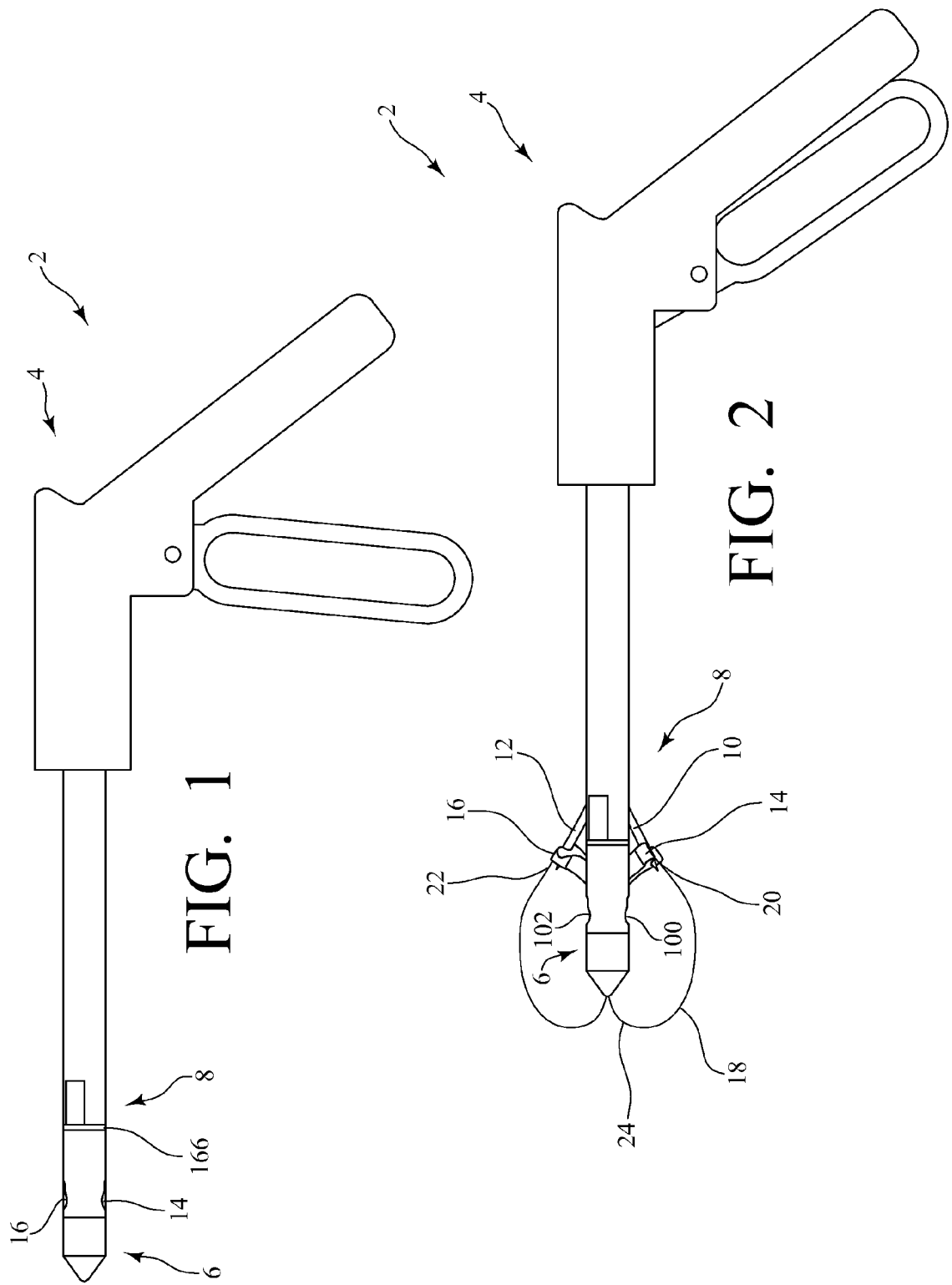

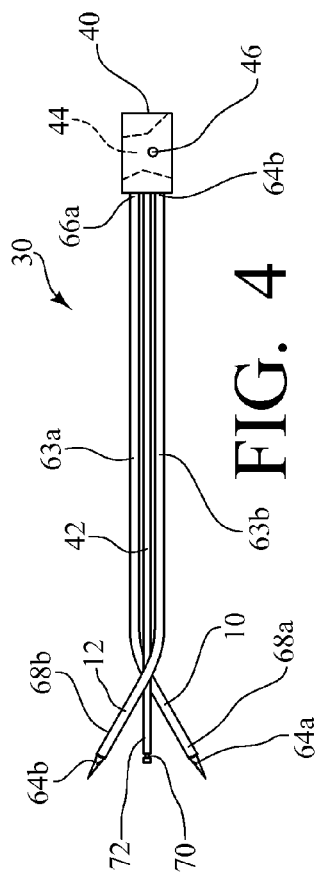
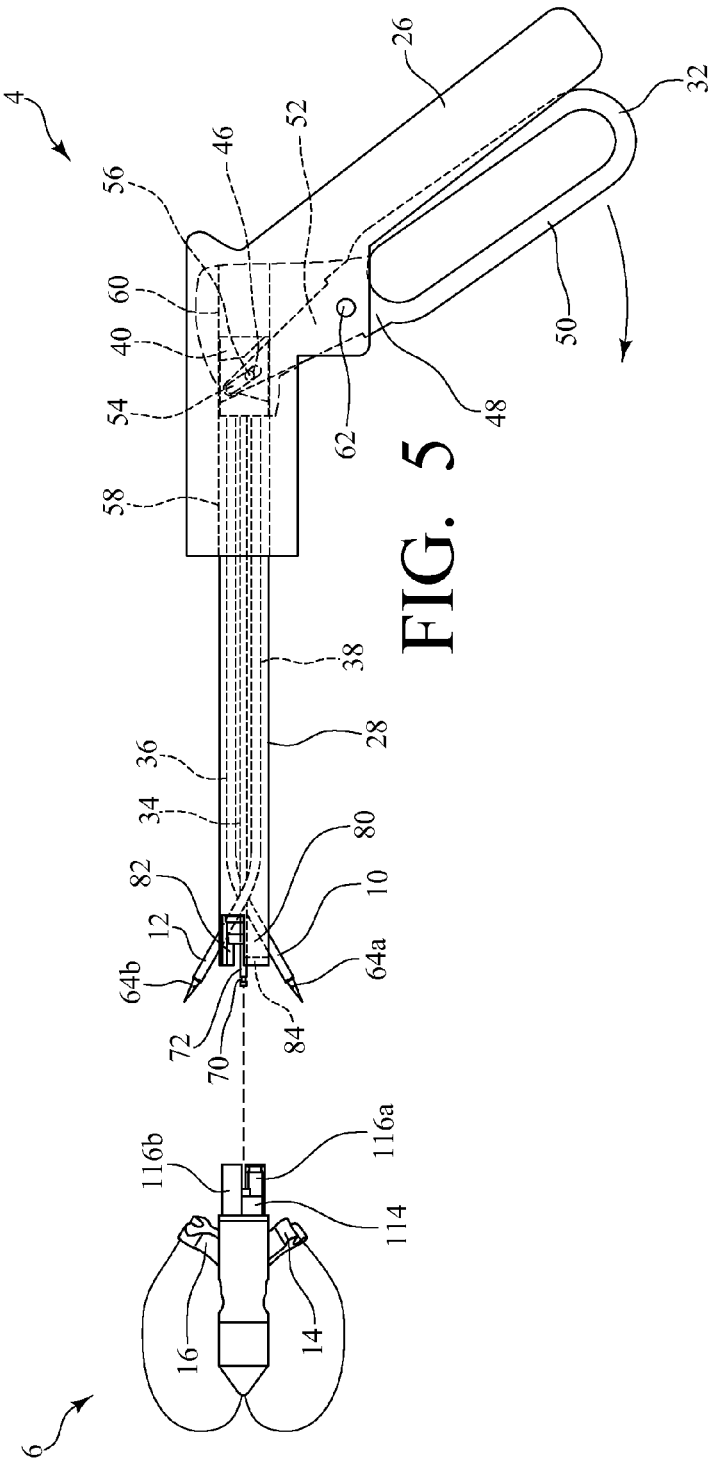

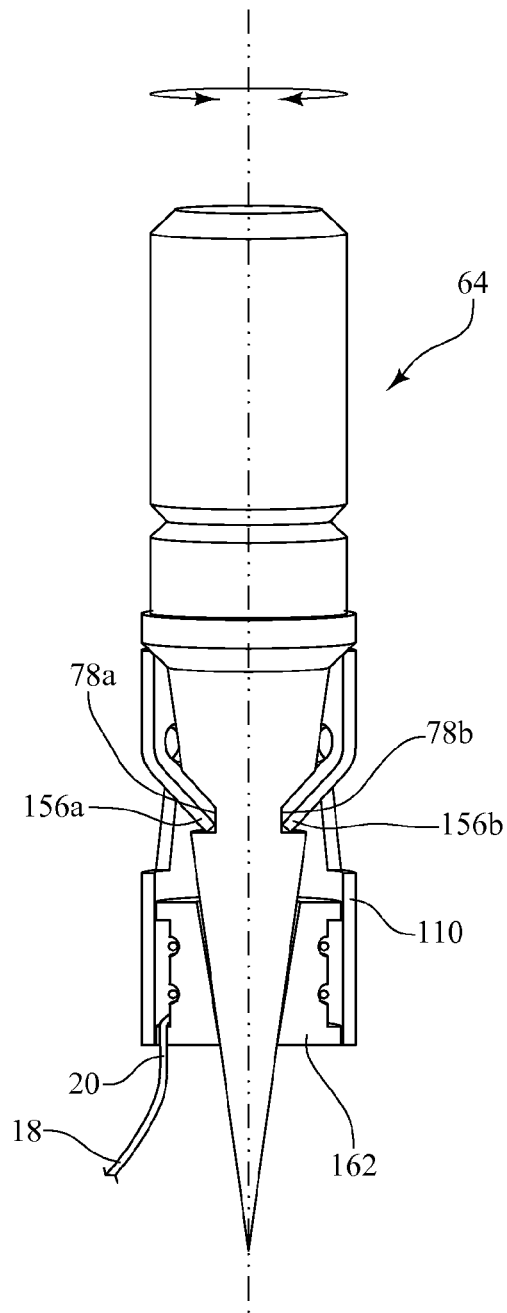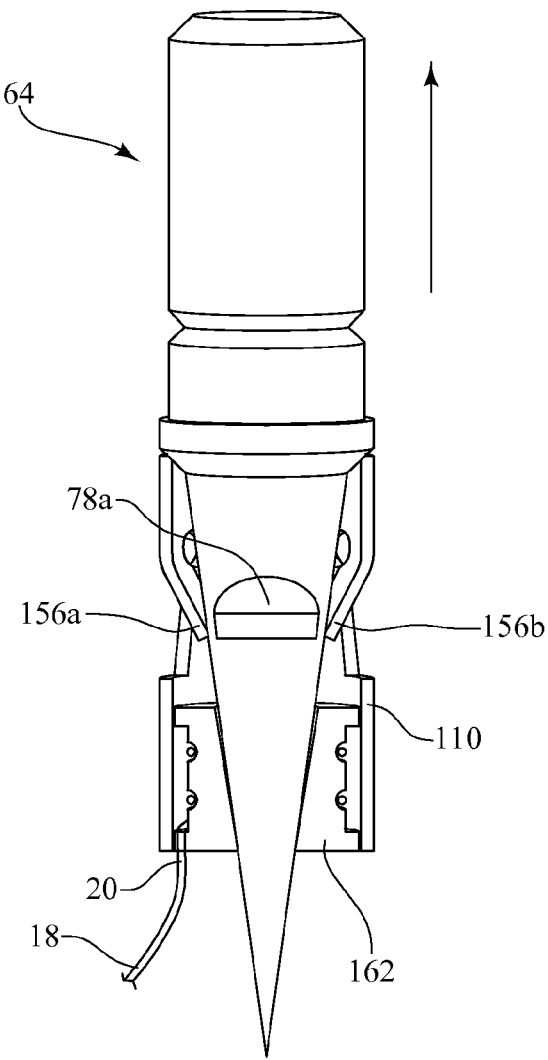
FIG. 21
FIG. 22

SUTURE INSTRUMENT AND METHOD

CROSS-REFERENCE TO RELATED APPLICATIONS

This application claims the benefit of U.S. Provisional Patent Application No. 61/129,781, filed Jul. 18, 2008, the entire disclosure of which is hereby incorporated by reference.

BACKGROUND OF THE INVENTION

1. Field of the Invention

The present invention relates to a system and method for inserting a stitch, or suture, through tissue around a hole in an abdominal muscle or a hollow organ, such as might be found in a patient following a laparoscopic surgery.

2. Description of Prior Art

During laparoscopic surgery, small incisions are required at multiple locations to provide access for the instruments which are to be used during the surgery. The incisions have an aperture of approximately ten millimeters (mm) in diameter and are located in the abdominal muscle and fascia, below the epidermis. The depth below the epidermis varies depending on the physical anatomy of the patient. Following surgery, most of the time, a suture is placed in the abdominal muscle adjacent the incision to prevent the formation of a hernia.

Currently, a conical device is used having a hole at a location on the surface of the tapered portion of the device. Another hole is located approximately 180 degrees from the first hole. The conical device is placed in the wound. A pointed device with a grasper on the tip is used to grasp one end of a suture, put it through the first hole in the fixture, through the abdominal muscle and fascia, and into the internal cavity. Once in the internal cavity, the surgeon locates the end of the device using a video camera tool, and grabs the suture using a different instrument located in a different port. The pointed device releases the suture and is then removed, inserted through the other hole, and through the abdominal muscle and fascia into the internal cavity. The surgeon then moves the end of the suture to the new location, where the end of the suture is transferred back to the grasper on the tip of the pointed device for extraction and tying. Obviously, this is a laborious and time-consuming process.

BRIEF SUMMARY OF THE INVENTION

In accordance with one aspect of the invention, a device for inserting a stitch through tissue around a hole in an abdominal muscle or a hollow organ includes: a body assembly and a suture cartridge assembly. The body assembly has a forward end, a first penetration member, and a second penetration member. The first penetration member and the second penetration member are actuated from retracted positions within the body assembly to deployed positions extending from the body assembly. The suture cartridge assembly is secured to the forward end of the body assembly. The suture cartridge assembly has a first arm member holding a first capture sleeve, a second arm member holding a second capture sleeve, and a suture cord having a first end attached to the first capture sleeve, a second end attached to the second capture sleeve and an intermediate portion between the first end and the second end. The first arm member and the second arm member are actuated from retracted positions in-line with the suture cartridge assembly to deployed positions for respectively receiving the first penetration member and the second penetration member.

A deployment means, in one action, simultaneously actuates the first arm member, the second arm member, the first penetration member, and the second penetration member such that the first penetration member and the second penetration member penetrate the tissue around the hole and extend into the first arm member and the second arm member, respectively. The first penetration member and the second penetration member become attached to the first capture sleeve and the second capture sleeve, respectively. In another action, the deployment means simultaneously retracts first arm member, the second arm member, the first penetration member and the second penetration member such that the first end and the second end of the suture cord are retracted with the first penetration member and the second penetration member, respectively, through the tissue and into the body assembly.

In accordance with one implementation, the suture cartridge assembly is separable from the body assembly, such that the body assembly is reusable with additional suture cartridge assemblies to insert additional stitches through tissue around additional holes in abdominal muscle or hollow organs following the use of the suture cartridge assembly to insert the stitch around the hole in the abdominal muscle or the hollow organ.

In accordance with another implementation, the body assembly further includes: a handle member; a barrel member extending forward from the handle member, a plunger assembly received within the barrel member and the handle member, a lever member, and a translation pin. The barrel member has a center rod receiving channel, a first penetration member receiving channel and a second penetration member receiving channel. The plunger assembly includes: a plunger head member having a longitudinal slot and translation pin receiving holes; a center rod member attached to the plunger head member and extending through the center rod receiving channel for actuating the first arm member and the second arm member. The first penetration member and the second penetration member are attached to the plunger head member and are respectively directed by the first penetration member receiving channel and the second penetration member receiving channel for respective engagement with the first arm member and the second arm member when actuated. The lever member has a central portion pivotally attached to the handle member, a first end extending externally from the handle member for user actuation, and a second end received within the handle member and within the longitudinal slot of the plunger head member. The second end of the lever member has a slot that is transverse to the longitudinal slot of the plunger head member. The translation pin slidingly attaching the plunger head member to the lever member, for translating rotational movement of the second end of the lever member to linear movement of the plunger assembly.

The first penetration member and the second penetration member may each include: a flexible shaft comprising a first end attached to the plunger head member and a forward end, and having an outer diameter; and a penetrating tip comprising a penetrating end and a connecting end, and having an outer diameter being substantially the same as the outer diameter of the flexible shaft, the penetrating end having a shallow taper coming to a sharp point, and parallel grooves each located on an opposite side of the penetrating end, the connecting end connected to the forward end of the flexible shaft. Further, each of the first capture sleeve and the second capture sleeve may include a tubular member having a side wall having opposing panels formed therein, the panels being folded inward such that as the penetrating tip extends into the capture sleeve the opposing panels deflect outwardly until reaching the parallel grooves, at which point the opposing panels engage the parallel grooves. Alternately, each of the first capture sleeve and the second capture sleeve comprises a tubular member having an peanut-shaped flexible clip bonded therein, such that as the penetrating tip extends into the capture sleeve the peanut-shaped flexible clip flexes outward until reading the parallel grooves, at which point the peanut-shaped flexible clip engages the parallel grooves.

In accordance with a further implementation, the suture cartridge assembly further includes: a cartridge body including a forward end, a connecting end, a first arm receiving cavity for receiving the first arm member on a first side of the cartridge body, a second arm receiving cavity for receiving the second arm member on a second side of the cartridge body, and an arm actuator receiving cavity having an opening at the connecting end; an arm actuator received within the arm actuator receiving cavity and cooperating with the first arm member, the second arm member, and the center rod member to actuate the first arm member and the second arm member from the retracted positions to the deployed positions and back to the retracted positions; and a suture spool assembly attached to the forward end of the cartridge body and comprising a spool member for holding the intermediate portion of the suture cord, and a shroud assembly covering the spool member and defining an opening for the first end and the second end of the suture cord to extend respectively from the spool member to the first capture sleeve and the second capture sleeve and for the intermediate portion of the suture cord to unwind from the spool member.

The barrel member may further have a forward end that defines a longitudinal alignment slot and a bore opening, and the connecting end of the cartridge body may include: a boss for mating with the bore opening of the forward end of the barrel member to provide axial alignment of the body assembly and the suture cartridge assembly; and an alignment member extending from the connecting end of the cartridge body for mating with the longitudinal alignment slot of the forward end of the barrel member to provide angular alignment of the body assembly and the suture cartridge assembly.

Further, the center rod member may have a forward end having a circumferential groove therein. The arm actuator may then include a connecting end, the connecting end being a boss defining a bore hole having a circumferential protrusion therein. The bore hole is for receiving the center rod member, with the circumferential protrusion serving as a detent to snap fit into the circumferential groove of the forward end of the center rod member for releasable engagement thereof.

Still further each of the first arm member and the second arm member may include a rotation head end, a capture sleeve end, and an extension portion therebetween. Each rotation head end may be rotatably connected to the cartridge body about a rotation point and having a radial slot radially aligned with the rotation point and a tracking boss protruding from an outboard side thereof. Each capture sleeve end may releasably hold a respective one of the first capture sleeve and the second capture sleeve. In this configuration, the arm actuator may include: a first side wall; a second side wall on an opposite side of the arm actuator from and parallel to the first side wall; a middle wall between the first side wall and the second side wall and parallel thereto; a first rod extending between the first side wall and the middle wall at a forward end of the arm actuator; a second rod extending between the second side wall and the middle wall at the forward end of the arm actuator; and a J-shaped tracking slot located on an interior surface of each of the first side wall and the second side wall. The first rod is received in the radial slot of the first arm member and the second rod is received in the radial slot of the second arm member for converting translational motion of the arm actuator into simultaneous rotational motion of the first arm member and the second arm member about each rotation point until each of the first arm member and the second arm member reaches a first attitude at which each tracking boss engages the respective J-shaped tracking slot to maintain the first attitude during further translational motion of the arm actuator.

In another aspect of the invention, a suture cartridge assembly for inserting a stitch through tissue around a hole in an abdominal muscle or a hollow organ comprises the suture cartridge described above.

In yet another aspect of the invention, a method for inserting a stitch through tissue around a hole in an abdominal muscle or a hollow organ includes: inserting into the hole a body assembly having penetration members that move from an in-line position to a deployed position, and a suture cartridge assembly secured to a forward end of the body assembly, the suture cartridge assembly having opposing arm members that move from an in-line position to a deployed position and each holding a capture sleeve to which an end of a suture cord is secured; simultaneously deploying the penetration members through the tissue around the hole and into the arm members such that the penetration members capture the capture sleeves; and simultaneously retracting the penetration members and the arm members such that the ends of the suture are retracted with the penetration members through the tissue around the hole and into the body assembly.

In accordance with one implementation, the body assembly further includes: a handle member; a plunger assembly received within a barrel member and the handle member, and a lever member. The plunger assembly includes a plunger head member, a center rod member attached to the plunger head member for actuating the opposing arm members, and the penetration members attached to the plunger head member. The lever member has a central portion pivotally attached to the handle member, a first end extending externally from the handle member for user actuation, and a second end received within the handle member and operable to push and pull the plunger assembly for translating rotational movement of the second end of the lever member to linear movement of the plunger assembly. The suture cartridge assembly further includes an arm actuator engaged by the center rod member. The structure being so, the method further includes: 1) squeezing the first end of the lever member toward the handle member to push the plunger assembly forward in the barrel member, such that the penetration members begin to advance from the body assembly, the center rod member causes the opposing arm members rotate to a predetermined attitude wherein a center line of each capture sleeve is coincident with a center line a respective penetration member, and the opposing arm members remain fixed at the predetermined attitude while the penetration members continue to advance within the respective opposing arm members a distance that causes the penetration members to engage the capture sleeves; and 2) extending the first end of the lever member away from the handle member to pull the plunger assembly toward the rear of the barrel member, such that the opposing arm members remain fixed at the predetermined attitude while the penetration members withdraw from the respective opposing arm members with the capture sleeves and the ends of the suture cord, the center rod member causes the opposing arm members to rotate to the in-line position within the suture cartridge assembly, and the penetration members, the capture sleeves, and the ends of the suture cord retract to the in-line position within the body assembly.

In accordance with yet another implementation, the penetration members include a penetrating tip comprising a penetrating end having a shallow taper coming to a sharp point, and parallel grooves each located on an opposite side of the penetrating end. Each of the capture sleeves comprises a tubular member having a side wall having opposing panels formed therein, the panels being folded inward such that as the penetrating tip extends into the capture sleeve the opposing panels deflect outwardly until reaching the parallel grooves, at which point the opposing panels engage the parallel grooves. Then, the method further includes, following retracing the penetration members and the arm members, removing the capture sleeves from the penetrating tips by rotating the penetrating tip 90 degrees in either direction such that the opposing panels are deflected outwardly to the tapered surfaces of the penetrating tip where the parallel grooves are not formed and pulling the penetrating tip from the capture sleeve such that the opposing panels slide along the tapered surface of the penetrating tip until becoming completely disengaged from the penetrating tip.

The invention will be better understood by reference to the following detailed description and the appended information.

BRIEF DESCRIPTION OF THE DRAWINGS

FIG. 1 is a side view of an exemplary device for inserting a stitch through tissue around a hole in an abdominal muscle or a hollow organ, according to the invention, shown prior to an actuation step.

FIG. 2 is a side view of the exemplary device of FIG. 1, following an actuation step.

FIG. 4 is side view of a plunger assembly of the exemplary device of FIG. 1.

FIG. 5 is an exploded side view of the exemplary device of FIG. 1 showing selected internal structure in broken line representation.

FIG. 21 is a side view with selected portions cut away showing the penetrating tip of FIG. 19 in engagement with the capture sleeve of FIG. 20.

FIG. 22 is a side view with selected portions cut away showing the penetrating tip of FIG. 19 in partial disengagement with the capture sleeve of FIG. 20.

DETAILED DESCRIPTION OF EXEMPLARY EMBODIMENTS OF THE INVENTION

Figure 3:
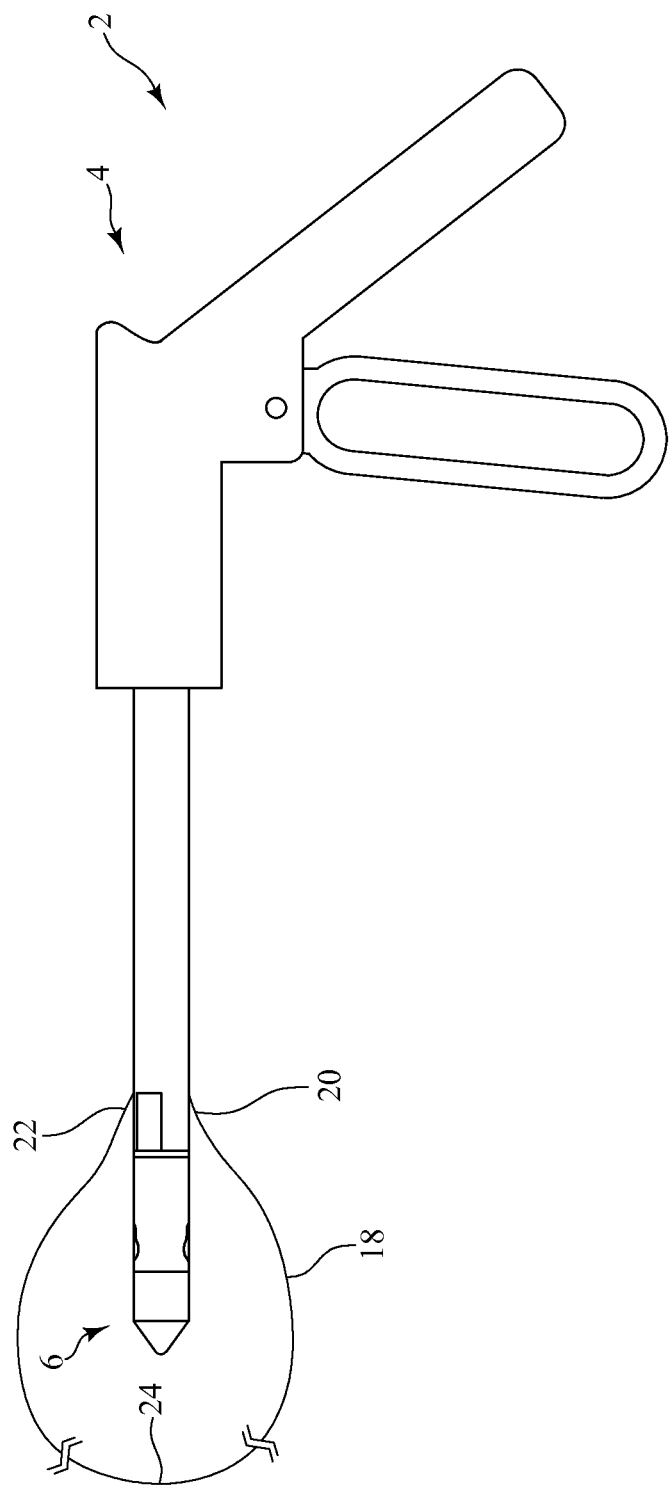
FIG. 3 is side view of the exemplary device of FIG. 1, following a retraction step.

FIG. 1 through FIG. 3 show an exemplary device 2 for inserting a stitch through tissue around a hole in an abdominal muscle or a hollow organ. The exemplary device 2 includes a body assembly 4 and a suture cartridge assembly 6.

The body assembly 4 has a forward end 8, a first penetration member 10, and a second penetration member 12. The first penetration member 10 and the second penetration member 12 are actuated from retracted positions within the body assembly 4, as shown in FIG. 1, to deployed positions extending from the body assembly 4, as shown in FIG. 2.

The suture cartridge assembly 6 is secured to the forward end 8 of the body assembly 4. The suture cartridge assembly 6 has a first arm member 14 holding a first capture sleeve (not shown), a second arm member 16 holding a second capture sleeve (not shown), and a suture cord 18 having a first end 20 attached to the first capture sleeve, a second end 22 attached to the second capture sleeve, and an intermediate portion 24 between the first end 20 and the second end 22. The first arm member 14 and the second arm member 16 are actuated from retracted positions in-line with the suture cartridge assembly 6, as shown in FIG. 1, to deployed positions, as shown in FIG. 2, for respectively receiving the first penetration member 10 and the second penetration member 12.

A deployment means in one action simultaneously actuates the first penetration member 10, the second penetration member 12, the first arm member 14, and the second arm member 16, such that the first penetration member 10 and the second penetration member 12 penetrate the tissue around the hole and extend into the first arm member 14 and the second arm member 16, respectively. The first penetration member 10 and the second penetration member 12 become attached to the first capture sleeve and the second capture sleeve, respectively.

In another action, the deployment means simultaneously retracts the first penetration member 10, the second penetration member 12, the first arm member 14, the second arm member 16, such that the first end 20 and the second end 22 of the suture cord 18 are retracted with the first penetration member 10 and the second penetration member 12, respectively, through the tissue and into the body assembly 4. FIG. 3 shows the exemplary device 2 following retraction of the first penetration member 10, the second penetration member 12, the first arm member 14, the second arm member 16 such that the first end 20 and the second end 22 of the suture cord 18 are retracted with the first penetration member 10 and the second penetration member 12, respectively, into the body assembly 4. The first arm member 14 and the second arm member 16 are retracted to positions in-line with the suture cartridge assembly 6.

As shown in FIG. 5, the suture cartridge assembly 6 is separable from the body assembly 4, such that the body assembly 4 is reusable with additional suture cartridge assemblies to insert additional stitches through tissue around additional holes in abdominal muscle or hollow organs following the use of the suture cartridge assembly to insert the stitch around the (first) hole in the abdominal muscle or the hollow organ.

Referring now to FIG. 4 and FIG. 5, the body assembly 4 further includes a handle member 26, a barrel member 28 extending forward from the handle member 26, a plunger assembly 30 received within the barrel member 28 and the handle member 26, and a lever member 32.

The barrel member 28 has a center rod receiving channel 34, a first penetration member receiving channel 36, and a second penetration member receiving channel 38. Preferably, the barrel member 28 is cylindrical and has a diameter substantially similar to the diameter of the hole (i.e., wound) (e.g., 10 mm diameter barrel for a 10 mm incision).

The plunger assembly 30 includes a plunger head member 40, a center rod member 42, and the first penetration member 10 and the second penetration member 12. The plunger head member 40 has a longitudinal slot 44 and a translation pin receiving hole 46. The center rod member 42 is attached to the plunger head member 40 and extends through the center rod receiving channel 34 for actuating the first arm member 14 and the second arm member 16. The first penetration member 10 and the second penetration member 12 are also attached to the plunger head member 40 and are respectively directed by the first penetration member receiving channel 36 and the second penetration member receiving channel 38 for respective engagement with the first arm member 14 and the second arm member 16 when actuated.

The center rod receiving channel 34, the first penetration member receiving channel 36, and the second penetration member receiving channel 38 are quasi-cylindrical cavities. The center lines of the three cavities lie on parallel longitudinal planes. The first penetration member receiving channel 36 and the second penetration member receiving channel 38 provide clearance and directional guidance for the first penetration member 10 and the second penetration member 12. These channels 36, 38 begin as straight cylindrical sections which then transition into a bend having a diameter increasing during the first half of the bend, and then decreasing back to the original diameter. The bend segments of the channels 36, 38 terminate into straight cylindrical sections that exit the sides of the barrel member 28 at an angle of approximately 30 degrees with respect to the longitudinal axis of the barrel member 28.

The lever member 32 has a central portion 48 pivotally attached to the handle member 26, a first end 50 extending externally from the handle member 26 for user activation, and a second end 52 received within the handle member 26 and within the longitudinal slot 44 of the plunger head member 30. The second end 52 of the lever member 32 has a slot 54 that is transverse to the longitudinal slot 44 of the plunger head member 40.

A translation pin 56 slidingly attaches the plunger head member 40 to the lever member 32.

Thus, the torsional force generated by squeezing the lever member 32 is transferred by the pivotal attachment of the lever member 32 to the handle member 26 into an axial force that drives the plunger assembly 40 in the forward direction via the conversion of the rotational motion of the second end 52 of the lever member 32 into linear motion of the plunger assembly 40 through the cooperation of the translation pin 56, the second end 52 of the lever member 32, and the plunger head member 40. This action simultaneously extends the first penetration member 10 and the second penetration member 12 through the fascia and the muscle. Extending the lever member 32 forward correspondingly retracts the plunger assembly 30. Additionally, the center rod member 42 is correspondingly extended and retracted.

As mentioned, the handle member 26 integrates the barrel member 28, the plunger assembly 30, and the lever 32. Concentric cylindrical bores 58, 60 provide alignment and positioning of the barrel member 28 and the plunger assembly 30 in the handle member 26. A pin 62 through the handle member 26 serves as the axis of rotation for the lever member 32 and is so located so that a given lever rotation angle provides the desired stroke of the plunger assembly 30.

The first penetration member 10 and the second penetration member 12 each comprise a flexible shaft 63a, 63b and a penetrating tip 64a, 64b. Each flexible shaft 63a, 63b includes a first end 66a, 66b attached to the plunger head member 40 and a forward end 68a, 68b and has an outer diameter. Each flexible shaft 63a, 63b may be a flexible rod or tube. One exemplary flexible shaft material is a polymide. Adding an internal spring provides more rigidity and helps to prevent kinking as the penetration member exits the barrel member. Each flexible shaft 63a, 63b must have a stiffness property to enable the respective penetration member 10, 12 to withstand the axial force required to penetrate the muscle and fascia without buckling.

The diameter of the plunger head member 40 is sized to be a slip fit within a longitudinal bore 60 formed in the handle member 26.

The center rod member 42 and the center rod receiving channel 34 are preferably coincident with a center line of the barrel member 28 and the plunger head member 40. A circumferential groove 70 at a forward end 72 of the center rod member 42 will be discussed in more detail below.

Each flexible shaft 63a, 63b may be attached to the plunger head member 40 through one or the other of two short rods (not shown) located on a forward end of the plunger head member 40. Each of the short rods are sized and located to fit within a respective flexible shaft 63a, 63b of the first penetration member 10 and the second penetration member 12. The short rods serve to further prevent the flexible shafts 63a, 63b from buckling during the penetration phase of the suture insertion cycle.

The longitudinal slot 44 of the plunger head member 40 provides clearance for the second end 52 of the lever member 32. Further, the translation pin receiving holes 46 in the plunger head member 40 are transverse to a longitudinal plane of the longitudinal slot 44. The translation pin 56 is received within the translation pin receiving holes 46 to mate the second end 52 of the lever member 32 with the plunger head member 40.

Figure 19:
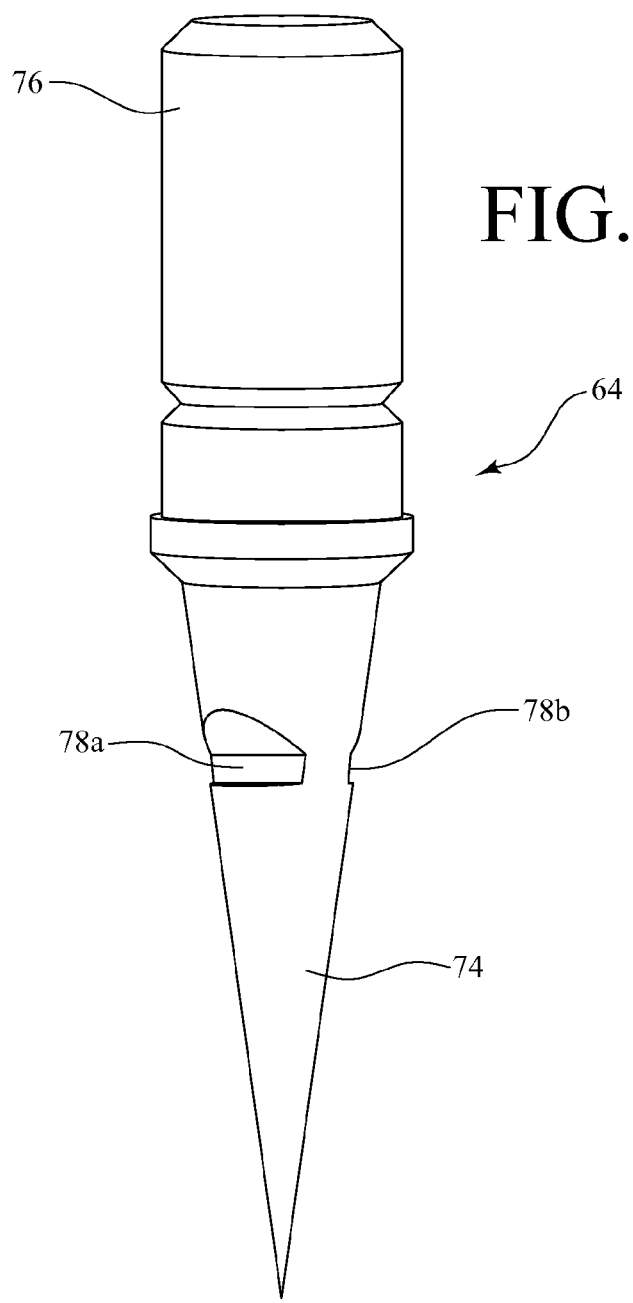
FIG. 19 is a perspective view of a penetrating tip of the exemplary device of FIG. 1.

Turning now to FIG. 19, the penetrating tip 64 includes a penetrating end 74 and a connecting end 76. The outer diameter of the penetrating tip 64 is substantially the same as the outer diameter of the flexible shaft 63. The penetrating end 74 has a shallow taper coming to a sharp point and parallel grooves 78a, 78b are formed on opposite sides of the penetrating end 74. The connecting end 76 is connected to the forward end 68 of the flexible shaft 63. Preferably, the diameter of the connecting end 76 is sized to be a slip fit with an inside diameter of the flexible shaft 63. The parallel grooves 78a, 78b, as discussed below, provide a means for attaching the captive sleeves and suture cord 18 to the penetrating tips 64.

Returning to FIG. 5, the barrel member 28 further has a forward end 80 that defines a longitudinal alignment slot 82 and a bore opening 84. In the exemplary embodiment, the barrel member 28 contains two longitudinal alignment slots 82.

Figure 6:
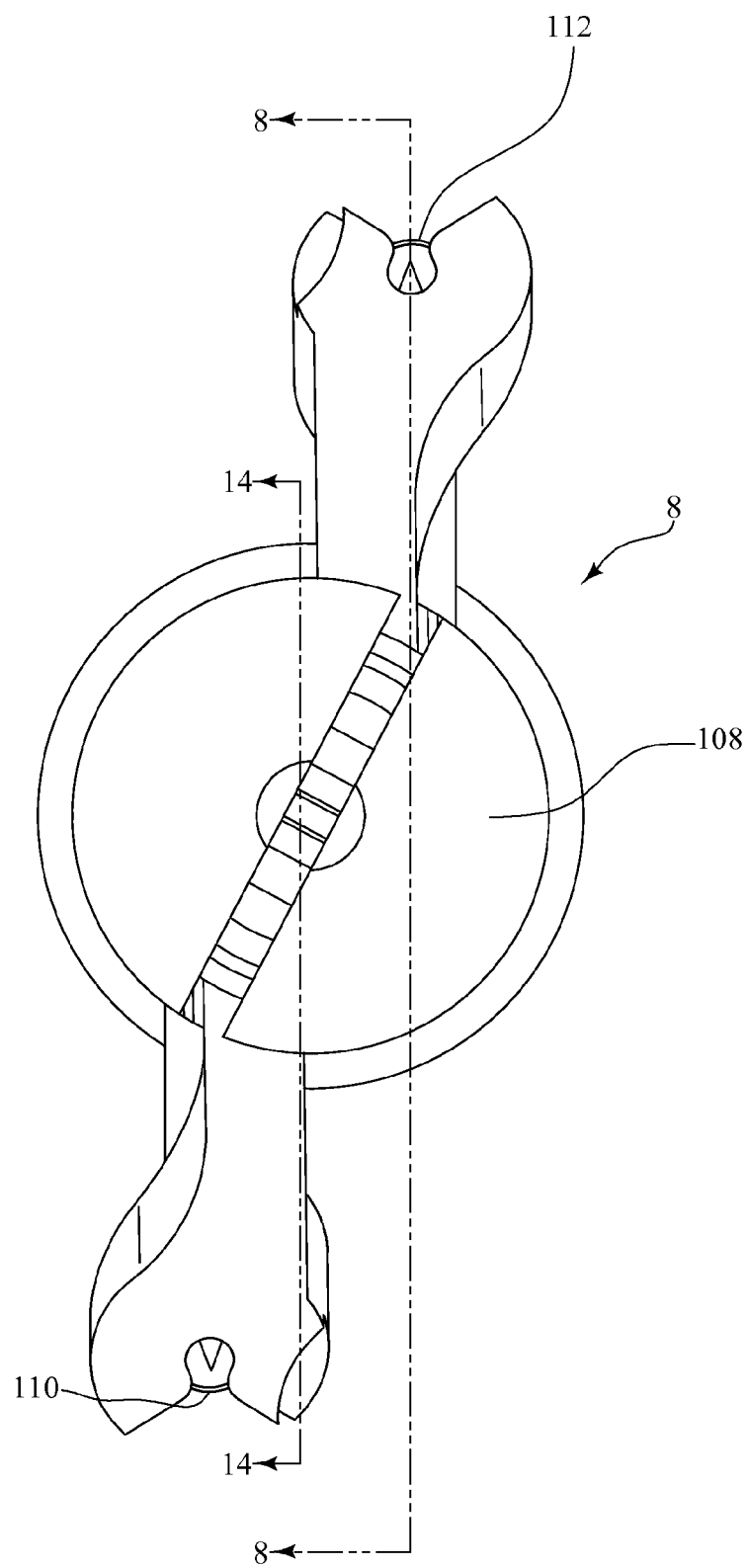
FIG. 6 is a front view of the exemplary device of FIG. 1, from a forward tip of a suture cartridge assembly looking back toward a body assembly of the exemplary device.
Figure 7:
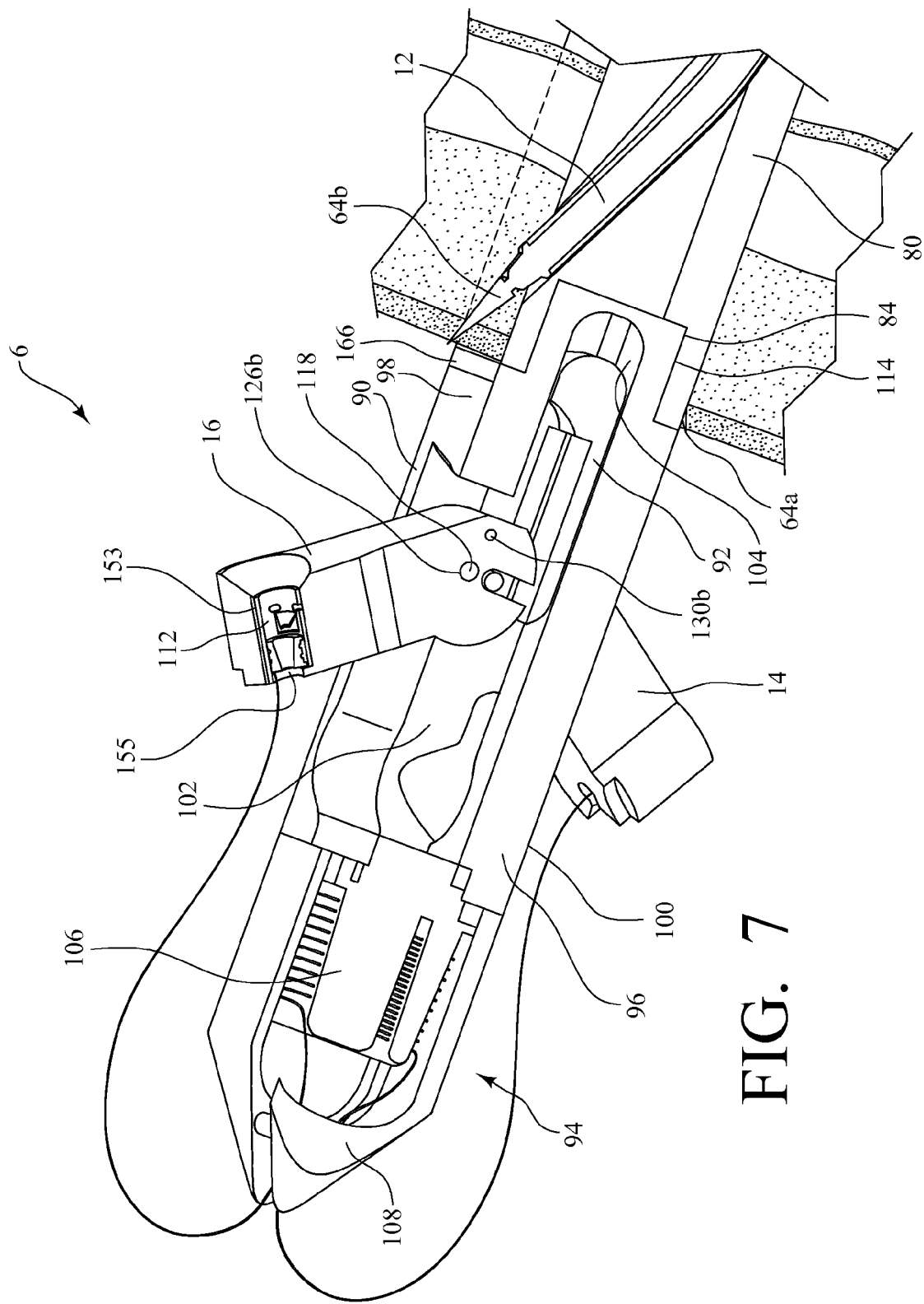
FIG. 7 is a partial perspective sectional view of the exemplary device of FIG. 1, shown during the actuation step, the section taken along the section line 8-8 as shown in FIG. 6.
Figure 8:
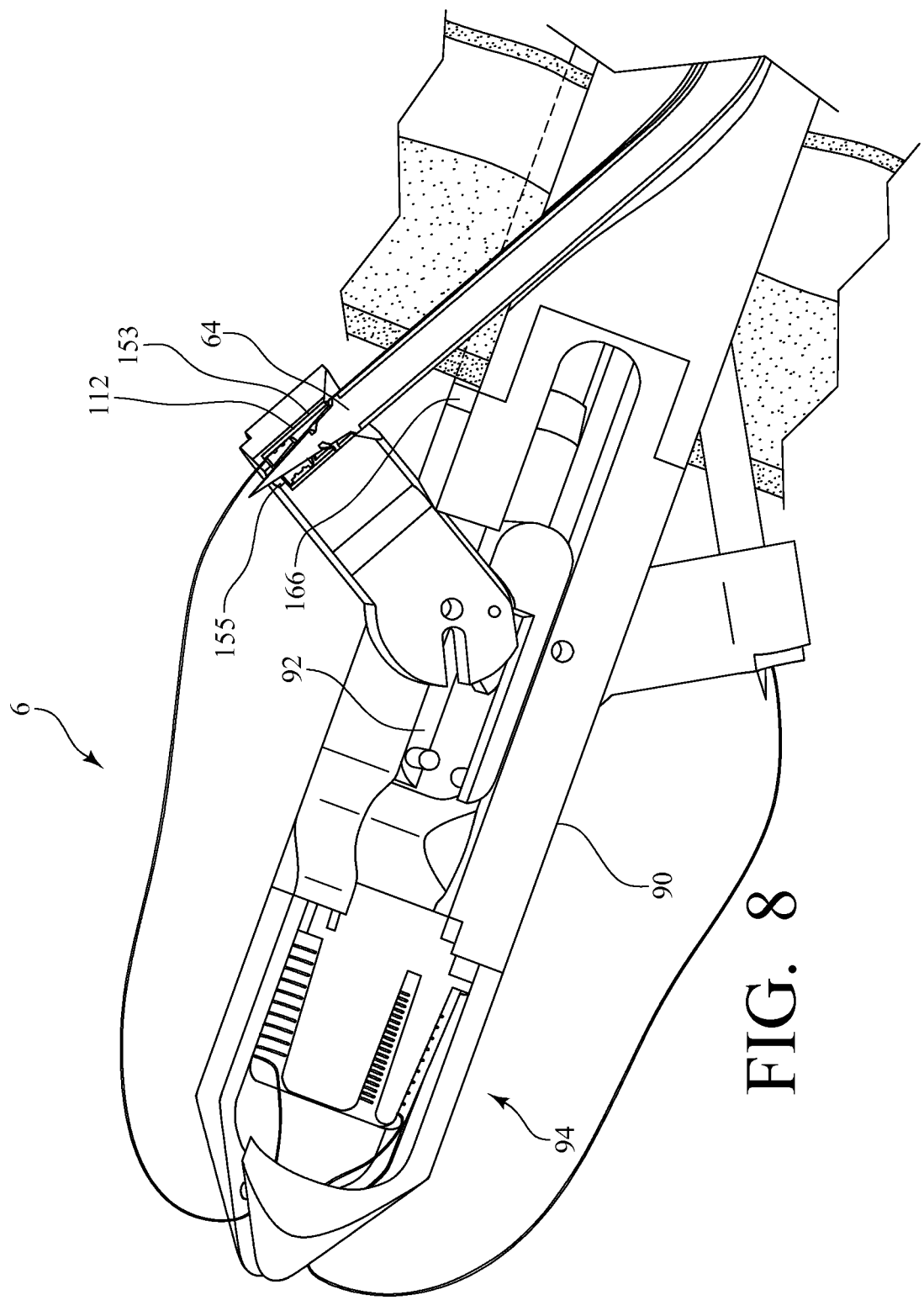
FIG. 8 is a is a partial perspective sectional view of the exemplary device of FIG. 1 taken along the section line 8-8 as shown in FIG. 6, shown following the actuation step.

As shown in FIG. 6, FIG. 7, and FIG. 8, the suture cartridge assembly 6 has a cartridge body 90, an arm actuator 92 and a suture spool assembly 94. The cartridge body 90 includes a forward end 96, a connecting end 98, a first arm receiving cavity 100 for receiving the first arm member on a first side of the cartridge body 90, a second arm receiving cavity 102 for receiving the second arm member on a second side of the cartridge body 90, and an arm actuator receiving cavity 104 having an opening at the connecting end 98. The arm actuator 92 is received within the arm actuator receiving cavity 104 and cooperates with the first arm member 14, the second arm member 16, and the center rod 42 to actuate the first arm member 14 and the second arm member 16 from the retracted positions to the deployed positions and back to the retracted positions. The suture spool assembly 94 is attached to the forward end 96 of the cartridge body 90 and includes a spool member 106 for holding the intermediate portion 24 of the suture cord 18, and a shroud assembly 108 covering the spool member 106 and defining an opening for the first end 20 and the second end 22 of the suture cord 18 to extend respectively from the spool member 106 to the first capture sleeve 110 and the second capture sleeve 112 and for the intermediate portion 24 of the suture cord 18 to unwind from the spool member 106.

The cartridge body 90 is preferably cylindrical in form and has a diameter equal to a diameter of the barrel member 28. The connecting end 98 of the cartridge body 90 includes a boss 114 for mating with the bore opening 84 of the forward end 80 of the barrel member 78 to provide axial alignment of the body assembly 4 and the suture cartridge assembly 6, and an alignment member 116 (FIG. 5) extending from the connecting end 98 of the cartridge body 90 for mating with the longitudinal alignment slot 82 of the forward end 80 of the barrel member 28 to provide angular alignment of the body assembly 4 and the suture cartridge assembly 6. In the exemplary embodiment, the connecting end 98 of the cartridge body 90 comprises two alignment members 116a, 116b (FIG. 5). The opening of the arm actuator receiving cavity 104 at the connecting end 98 of the cartridge body 90 provides access for the center rod member 42 to extend into the suture cartridge assembly 6. The cartridge body 90 includes internal walls parallel to a center line of the cartridge body 90 and defining the arm actuator receiving cavity 104, and further providing both longitudinal and angular alignment for the arm actuator 92.

The first arm receiving cavity 100 and the second arm receiving cavity 102 accommodate the first arm member 14 and the second arm member 16, respectively, when in a stowed position during insertion and retraction from the hole (i.e., the wound). Parallel longitudinal surfaces in each of the first arm receiving cavity 100 and the second arm receiving cavity 102 establish the lateral location of the first arm member 14 and the second arm member 16. Cylindrical through holes perpendicular to the parallel longitudinal surfaces of the first arm receiving cavity and the second arm receiving cavity, provide for cartridge arm rotation pins 118.

Figure 9:
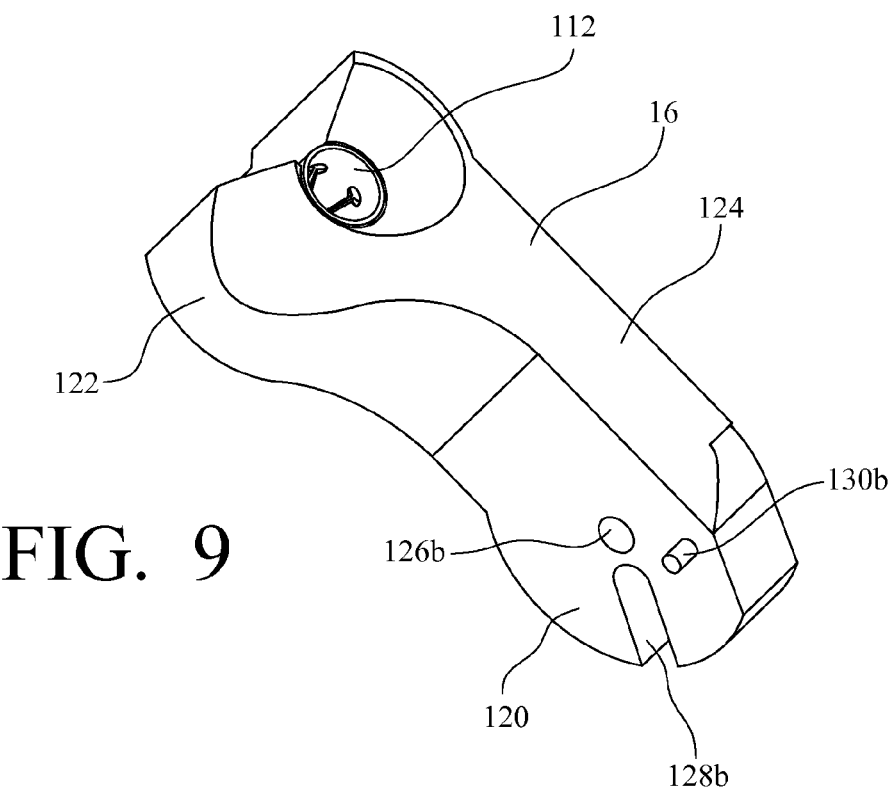
FIG. 9 is a perspective view of first arm member of the exemplary device of FIG. 1.

As shown in FIG. 9, each of the first arm member 14 (NOT SHOWN) and the second arm member 16 (SHOWN) includes a rotation head end 120, a capture sleeve end 122, and an extension portion 124 there between. Each rotation head end 120 rotatably connects to the cartridge body 90 about a rotation point 126 (i.e., the cartridge arm rotation pin 118) and has a radial slot radially aligned with the rotation point 126, and a tracking boss 130 protruding from an outboard side thereof. Each capture sleeve end 122 releasably holds a respective one of the first capture sleeve 110 (NOT SHOWN) and the second capture sleeve 112 (SHOWN).

Returning to FIG. 7 and FIG. 8, a plane of rotation of the first arm member 14 is in alignment with a plane of movement of the first penetration member 10, and a plane of rotation of the second arm member 16 is in alignment with a plane of movement of the second penetration member 12. The alignment member 116 (FIG. 5) of the connecting end 98 of the cartridge body 90 is received within the longitudinal alignment slot 82 of the forward end 80 of the barrel member 28 to ensure alignment of these planes. Additionally, a radial groove 132 (FIG. 5) on an inside surface at a connecting end of each of the alignment members 116 mates with a raised surface 134 (FIG. 5) located within the longitudinal alignment slot 82 of the forward end 80 of the barrel member 28 to form a locking detent and prevent unintentional separation of the suture cartridge assembly 6 from the body assembly 4.

Figure 10:
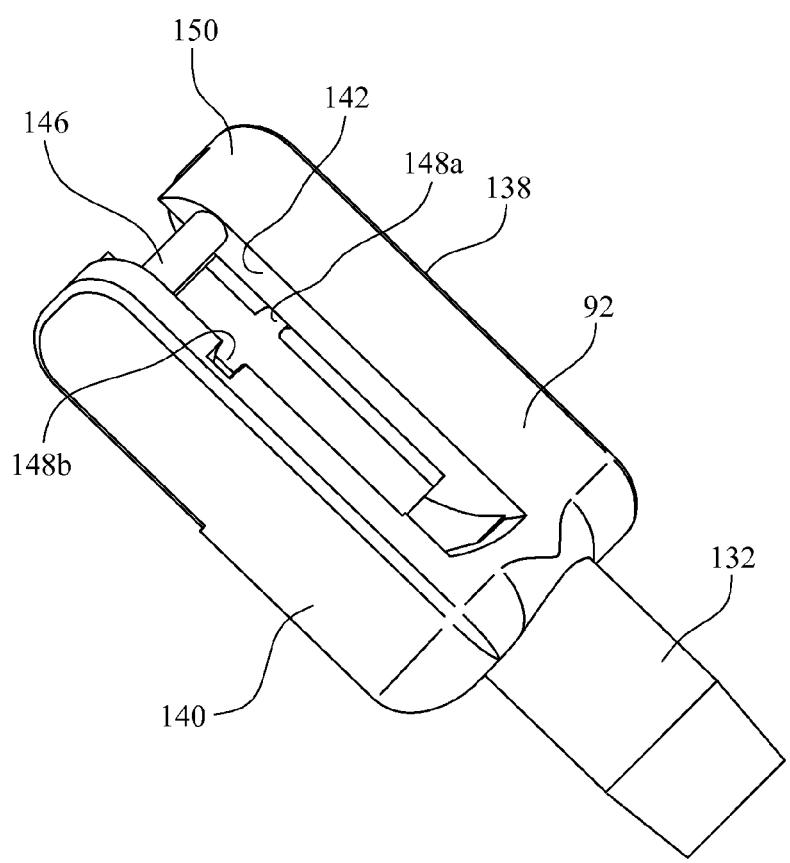
FIG. 10 is a perspective view of a arm actuator of the exemplary device of FIG. 1.
Figure 11:
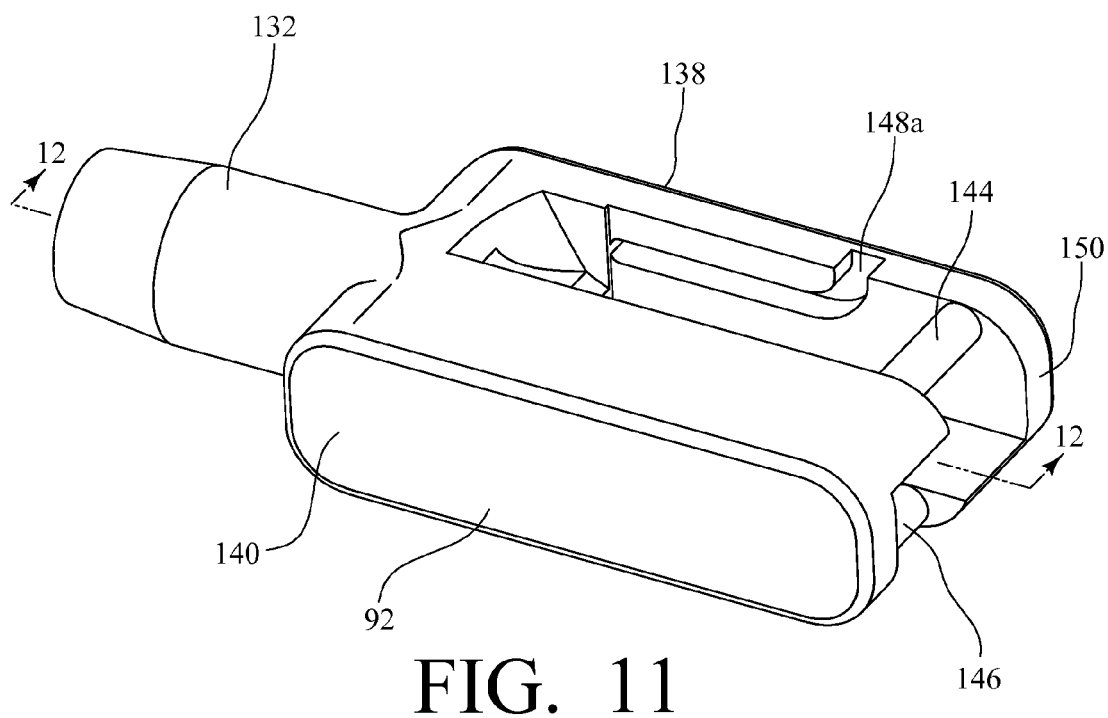
FIG. 11 is a another perspective view of the arm actuator of FIG. 10.
Figure 12:
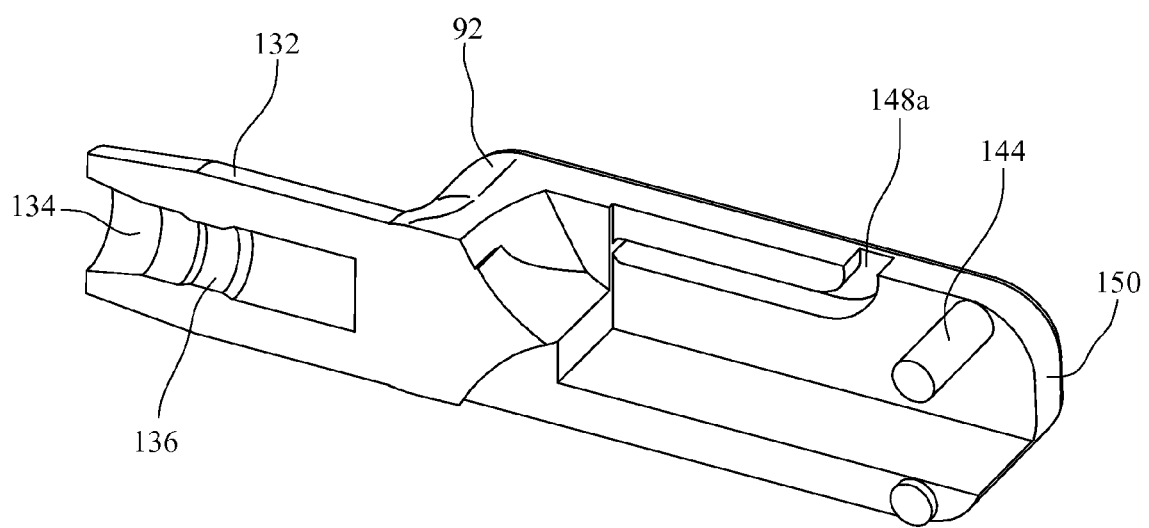
FIG. 12 is a perspective sectional view of the arm actuator of FIG. 11 taken along the line 12-12.

Turning now to FIG. 10 through FIG. 12, the arm actuator 92 has a connecting end 132 that is a boss and defines a bore hole 134 having a circumferential protrusion 136 therein. The bore hole 134 is for receiving the center rod member 42 and the circumferential protrusion 136 serves as a detent to snap fit into the circumferential groove 70 of the forward end 72 of the center rod member 42 for releasable engagement thereof. The arm actuator 92 further includes a first side wall 138, a second side wall 140, a middle wall 142 (FIG. 10), a first rod 144, a second rod 146, and a J-shaped tracking slot 148a, 148b located on an interior surface of each of the first side wall 138 and the second side wall 140. The second side wall 140 is on an opposite side of the arm actuator 92 from and parallel to the first side wall 138. The middle wall 142 is between the first side wall 138 and the second side wall 140 and is parallel thereto. The first rod 144 extends between the first side wall 138 and the middle wall 142 at a forward end 150 of the arm actuator 92. The second rod 146 extends between the second side wall 140 and the middle wall 142 at the forward end 150 of the arm actuator 92. The connecting end 132, the first side wall 138, and the second side wall 140 of the arm actuator 92 maintain the orientation of the arm actuator 92 within the arm actuator receiving cavity 140 of the cartridge body 90.

Figure 13:
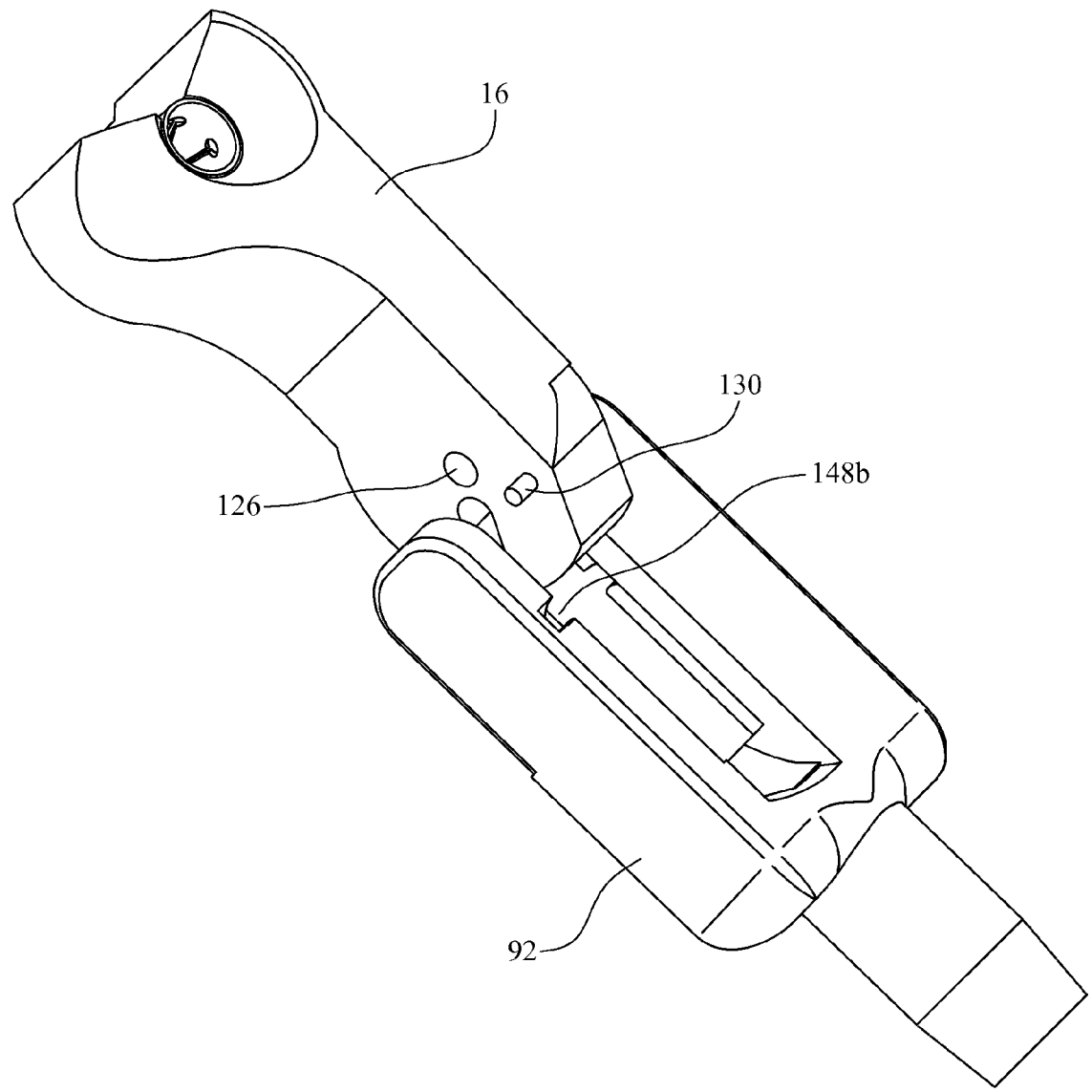
FIG. 13 is a perspective view of the first arm member of FIG. 9 in mating cooperation with the arm actuator of FIG. 10.
Figure 14:
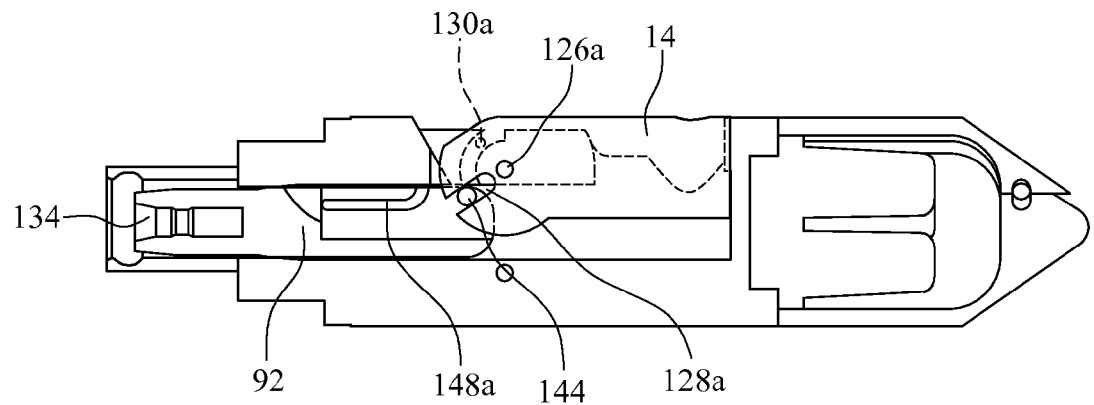
FIG. 14-FIG. 18 are side sectional views of the suture cartridge assembly of the exemplary device of FIG. 1 shown at various points in the actuation step and along the section line 14-14 as shown in FIG. 6.
Figure 15:
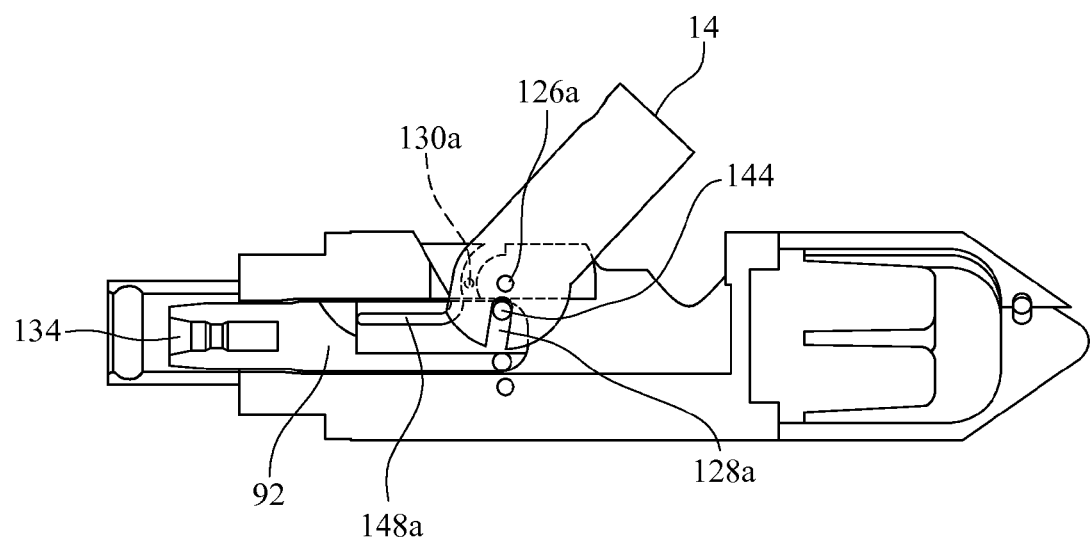
Figure 16:
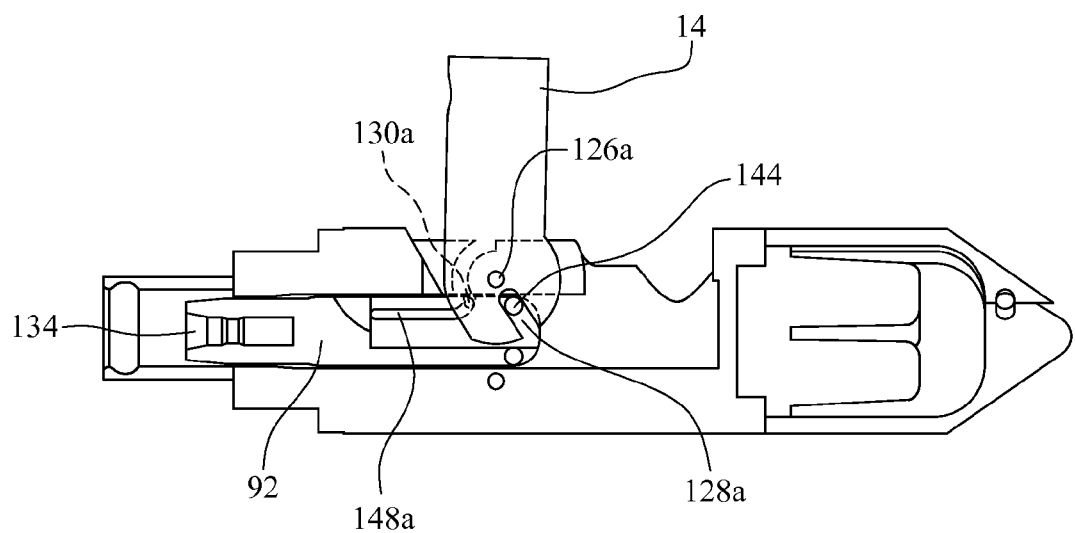
Figure 17:
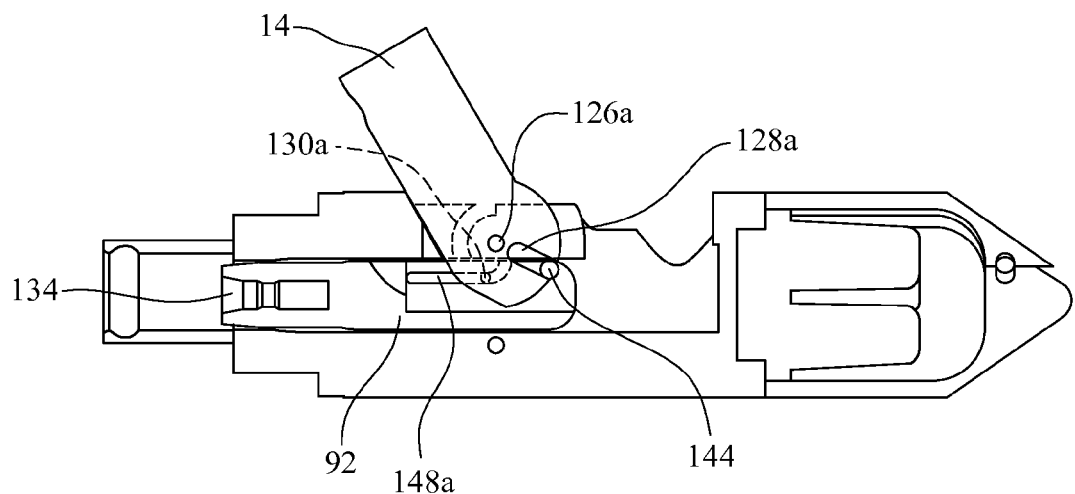
Figure 18:
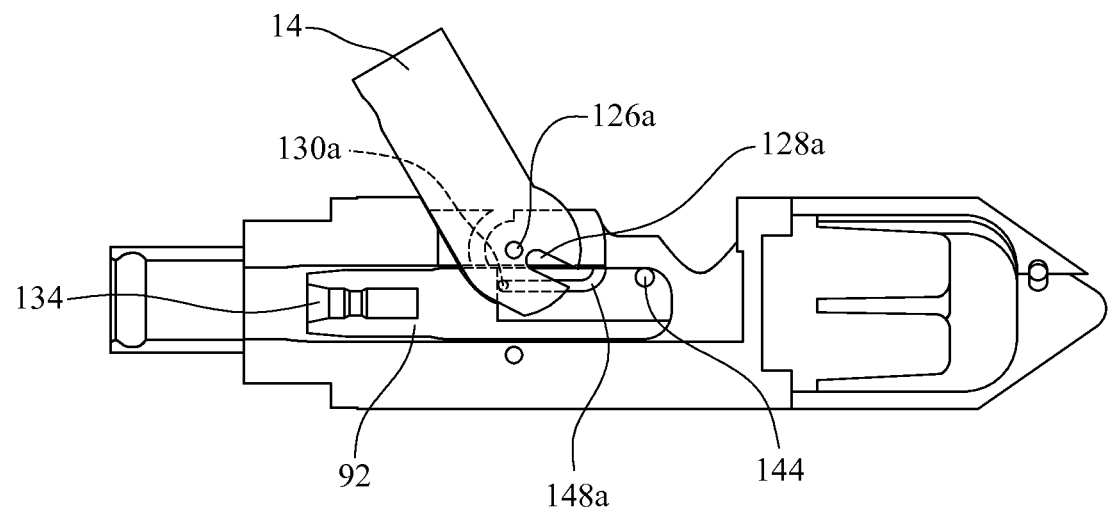

As shown in FIG. 13 with respect to the second arm member 16 only, the second rod 146 is received in the radial slot 128b of the second arm member 16. Not shown in FIG. 13, but understood, the first rod is received in the radial slot 128a of the first arm member 14.

As shown in FIG. 14 through FIG. 18, the configuration of the first arm member 14, the second arm member 16, and the arm actuator 92 converts translational motion of the arm actuator 92 into simultaneous rotational motion of the first arm member 14 and the second arm member 16 about each rotation point 126a, 126b until each of the first arm member 14 and the second arm member 16 reaches a first attitude, which in the exemplary embodiment is about 120 degrees from the starting position. At the first attitude, each tracking boss 130a, 130b engages the respective J-shaped tracking slot 148a, 148b to maintain the first attitude during further translational motion of the arm actuator 92.

Figure 20:
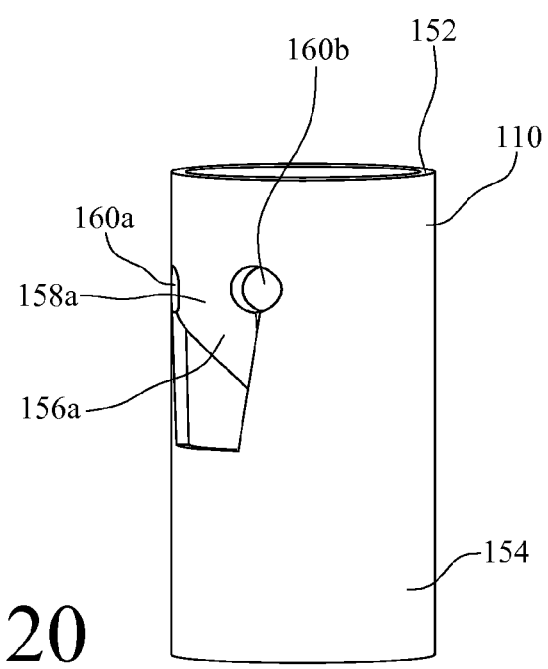
FIG. 20 is a perspective view of a capture sleeve according to one embodiment of the exemplary device of FIG. 1.

The center rod member 42 enters the bore hole 134 of the cartridge arm actuator 92 during a syringe compression stroke and forces the arm actuator 92 to translate in the forward direction. During a retraction stroke or extension of the first end of the lever member 32 from the handle member 26, the center rod member 42 pulls the arm actuator 92 back to its initial position, thereby enabling the arm members 14, 16 to be rotated back to the initial position thereof. As shown in FIG. 20, in one embodiment, each of the first capture sleeve 110 and the second capture sleeve 112 (not shown) comprises a tubular member 152 having a side wall 154 having opposing panels 156a, 156b formed therein. The panels 156a, 156b are folded inward along hinge portions 158a, 158b such that as the penetrating tips 64 extend into the respective capture sleeves, the opposing panels 156a, 156b deflect outwardly until reaching the parallel grooves 78a, 78b, at which point the opposing panels 156a, 156b return to their inwardly folded position to engage the parallel grooves 78a, 78b. The capture sleeves 110, 112 must be oriented within the capture sleeve end 122 of the arm member 14, 16 so that the opposing panels 156a, 156b will mate with the parallel grooves 78a, 78b in the penetrating tips 64.

As shown in FIG. 7 and FIG. 8, the capture sleeves 110, 112 are a slip fit in a capture sleeve bore 153 of the capture sleeve end 122 of the arm member 14, 16 at a retaining flange 155 at a bottom of the capture sleeve bore 153 retains the capture sleeves 110, 112 in order to prevent the capture sleeves 110, 112 from being forced out the bottom during mating with the penetrating tips 64.

FIG. 21 shows a penetrating tip 64 and such a capture sleeve 110 in such engagement. Thus, the material from which the capture sleeves 110, 112 of this embodiment are fabricated should be cuttable and foldable, yet resilient with respect to the inwardly folded panels 156a, 156b. To aid in the resilience of the panels 156a, 156b, relief holes 160a, 160b may be formed along the hinge portion 158a, 158b. As shown in FIG. 22, advantageously, removal of the penetrating tip 64 from the capture sleeve 110 is facilitated by merely rotating the penetrating tip 90 degrees in either direction such that the opposing panels 156a, 156b are deflected outwardly to the tapered surfaces of the penetrating tip 64 where the parallel grooves 78a, 78b are not formed. The penetrating tip 64 may then be pulled apart from the capture sleeve 10 such that the opposing panels 156a, 156d slide along the tapered surface of the penetrating tip 64 until becoming completely disengaged from the penetrating tip 64.

Figure 23:
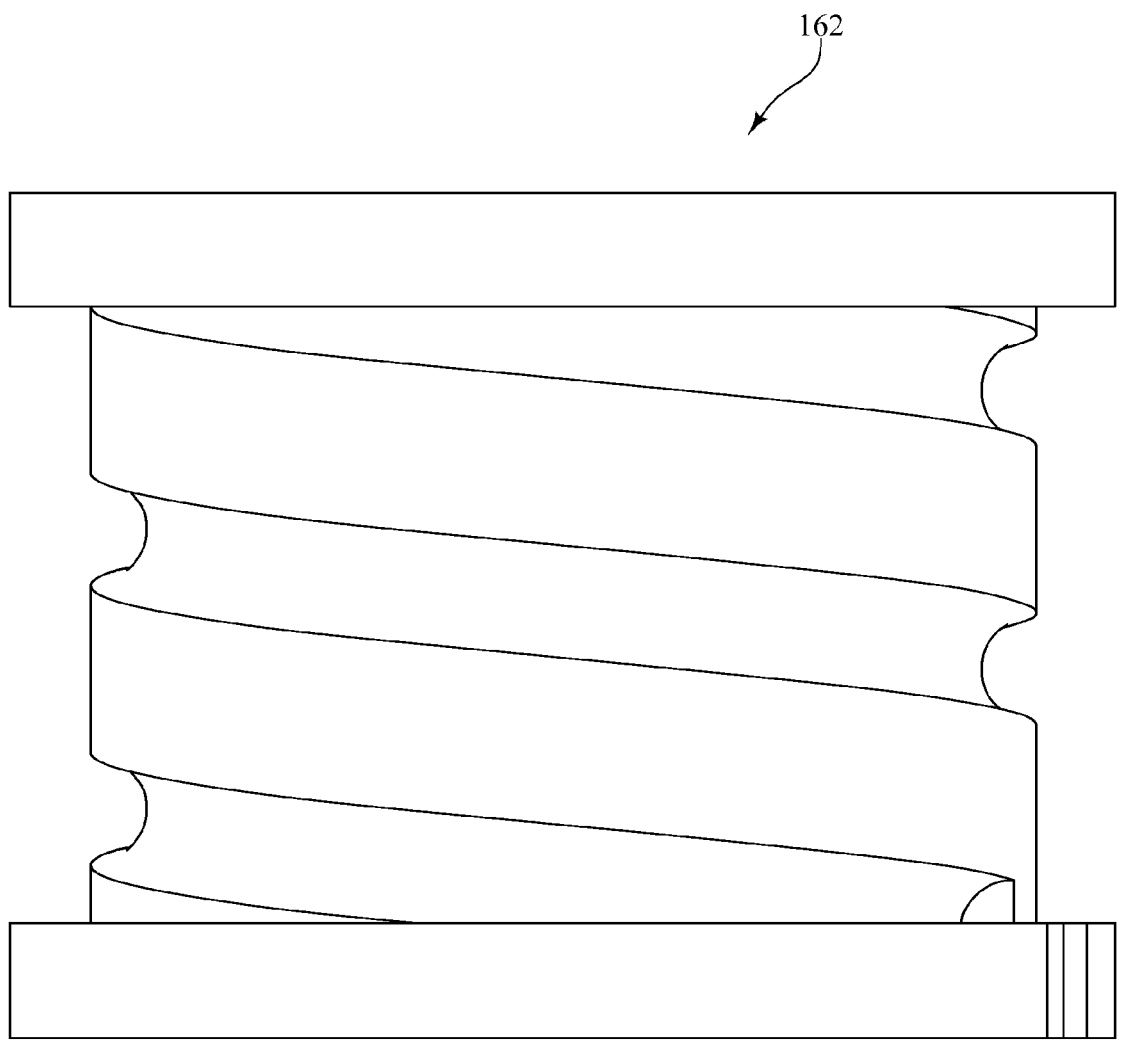
FIG. 23 is a side view of a cord retainer of the exemplary device of FIG. 1.

Referring now to FIG. 21, FIG. 22, and FIG. 23, a cord retainer member 162 is included at a forward end of the capture sleeve 110 for attaching the respective first end 20 and second end 72 of the suture cord 18 to a capture sleeve 110, 112. The cord retainer 162 is preferably a spool-shaped member having a helical groove around an outer surface thereof and a tapered hole along a longitudinal axis thereof for receiving the penetrating tip 64 of the respective penetration member 10, 12. The respective first end 20 and second end 22 of the suture cord 18 may be wrapped in the helical grooves and bonded along with the cord retainer 162 in the capture sleeve 110, 112 thereto with an adhesive or the like.

Figure 24:
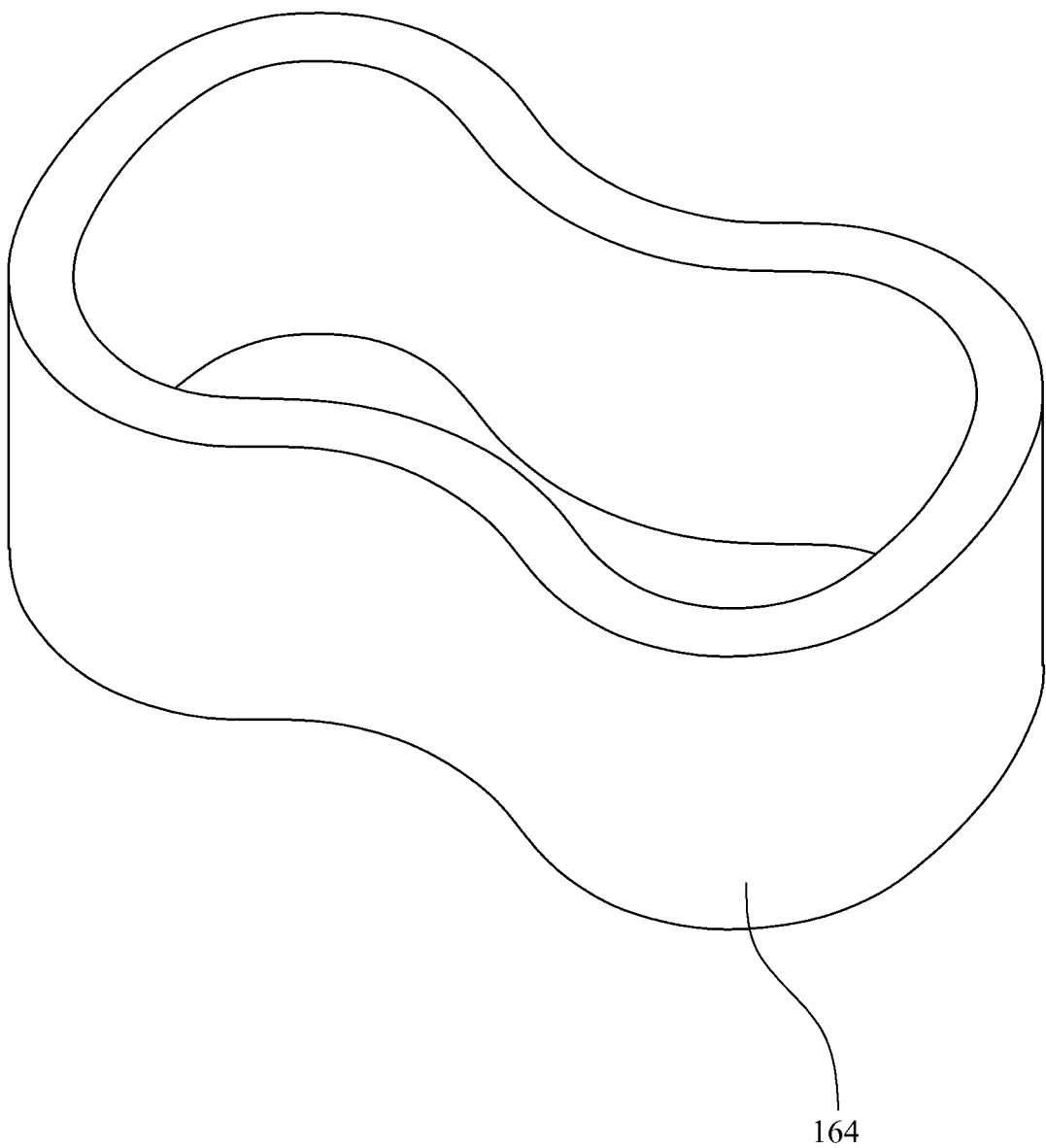
FIG. 24 is a perspective view of a peanut-shaped flexible clip according to another embodiment of the exemplary device of FIG. 1.
Figure 25:
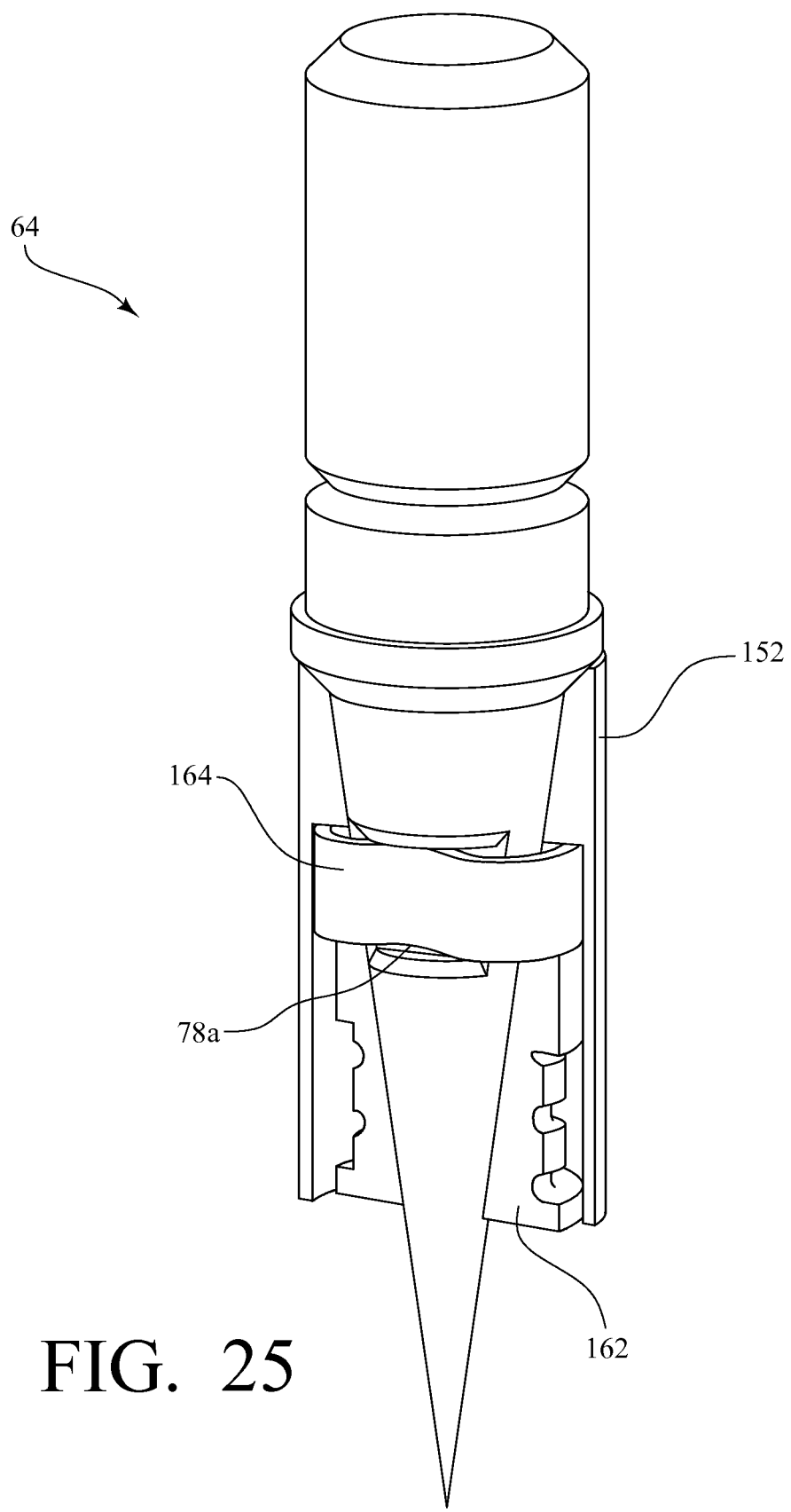
FIG. 25 is a perspective view with selected portions cut away of the peanut-shaped flexible clip bonded in a capture sleeve of the another embodiment of the exemplary device of FIG. 1.

In an alternate embodiment, shown in FIG. 24 and FIG. 25, each of the first capture sleeve 110 and the second capture sleeve 112 also comprises a tubular member 152, but has a peanut-shaped flexible clip 164 bonded therein, such that as the penetrating tip 64 extends into the capture sleeve 110, the peanut-shaped flexible clip 164 flexes outward until reaching the parallel grooves 78a, 78b, at which point the peanut-shaped flexible clip 164 engages the parallel groups. The disengagement of the penetrating tip 64 from the capture sleeve 110 would be in a like manner as described above. Further, the peanut-shaped flexible clip 164 would necessarily have resilient properties. Further, it is noted that the cord retainer 162 described above could also be used in conjunction with this alternate embodiment.

When the first arm member 14 and the second arm member 16 are positioned at approximately the 120 degrees attitude, a center line of the first capture sleeve 110 and the second capture sleeve 112 is coincident with a center line of each of the first penetration member 10 and the second penetration member 12, respectively (FIG. 8).

As shown in FIG. 7 through FIG. 9, and FIG. 13, the capture sleeve ends 122 of each of the first arm member 14 and the second arm member 16 have a conical surface at an entry position to the capture sleeve ends 122. The diameter of the capture sleeve bore 153 (FIG. 7, FIG. 8) bore is to be a slip fit with the capture sleeves 110, 112. The retaining flange 155 (FIG. 7, FIG. 8) at the bottom of the capture sleeve bore 153 is provided to retain the capture sleeves 110, 112 from being pushed out the bottom during mating with the penetrating tip 64. A segment of a cylindrical wall that forms the bore is removed to facilitate the release of the suture cord 18 from the arm members 14, 16.

The outside diameter of the capture sleeves 110, 112 must be equal to or less than the outer diameter of the respective flexible shafts 63a, 63b. Preferably, the outer diameter of the capture sleeves 110, 112 is equal to the outer diameter of the flexible shafts 63a, 63b. Additionally, the capture sleeves 110, 112 must abut the connecting ends of the penetrating tips 64 with the capture sleeves 110, 112 engaged with the penetrating tips 64. These cooperations facilitate retraction of the first penetration member 10, the second penetration member 12, the first capture sleeve 14, the second capture sleeve 16, the first end 20 of the suture cord 18, and the second end 22 of the suture cord 18 through the tissue around the hole (i.e., wound) and into the body assembly 4 for removal.

Advantageously, the configuration of the suture cartridge assembly 6 allows deployment of the first arm member 14 and the second arm member 16 to a position where the center lines of the first capture sleeve 110 and the second capture sleeve 112 are aligned with the center lines of the first penetration member 10 and the second penetration member 12 prior to arrival of the respective penetrating tip 64 at the entrance of the respective capture sleeve 110, 112. Further, the first arm member 14 and the second arm member 16 are then maintained at the required attitude while the respective penetrating tips 64 advance into and engage the respective capture sleeves 110, 112. The required attitude is further maintained during the retraction phase until the respective penetrating tips 64 have cleared the respective arm members 14, 16, at which point the arm members 14, 16 and the penetration members 10, 12 simultaneously retract into the respective suture cartridge assembly 6 and body assembly 4 for removal from the hole (i.e., wound).

In use, the exemplary suture instrument 10 is inserted into the wound to a depth that makes the indicator line 166 (FIG. 1, FIG. 7, and FIG. 8), located on the cartridge body 90, visible via a fiber optic laparoscopic video instrument.

User actuation of the first end 50 of the lever member 32 extending externally from the handle member 26 (i.e., squeezing the lever member 32 to the handle member 26) forces the first penetration member 10 and the second penetration member 12 to penetrate the tissue around the wound and to deploy the first arm member 14 and the second arm member 16 into position. More specifically, the center rod member 42 forces the arm actuator 92 in a forward direction, which engages the radial slot 128 in each of the first arm member 14 and the second arm member 16 and produces the rotation of the first arm member 14 and the second arm member 16 to the required attitude wherein the center line of each capture sleeve 110, 112 is coincident with the center line of a respective penetrating tip 64. Each of the first arm member 14 and the second arm member 16 then remains fixed at this attitude while each respective penetrating tip 64 continues to be extended within the respective capture sleeve 110, 112 a distance that causes the respective penetrating tips 64 to engage the respective capture sleeves 110, 112. This alignment occurs at the end of the compression stroke of the lever member 32 and produces the connection of the respective capture sleeves 110, 112 to the first penetration member 10 and the second penetration member 12. The first end 20 and the second end 22 of the suture cord 18 also being connected to the respective capture sleeves 110, 112, the respective ends 20, 22 of the suture cord 18 are also connected to the respective first penetration member 10 and the second penetration member 12.

The first end 50 of the lever member 32 extending externally from the handle member 26 is then extended to its original position which retracts the first penetration member 10, the second penetration member 12, the first capture sleeve 110, the second capture sleeve 112, the first end 20 of the suture cord 18, and the second end 22 of the suture cord 18 completely within the body assembly 4. Further, the center rod member 42 is simultaneously retracted, pulling the arm actuator 92 to its initial position and retracting the first arm member 14 and the second arm member 16 back into the cartridge body 90.

The exemplary device 2 is then retracted from the wound, with each end 20, 22 of the suture cord 18 attached to a respective one of the first penetration member 10 and the second penetration member 12, and causing the intermediate portion 24 of the suture cord 18 to be pulled from the spool member 106 where it had been stored. When the device 2 is fully retracted from the wound, both ends 20, 22 of the suture cord 18 are external to the wound. The suture cord 18 is then in the form of a loop that runs down through one side of the wound and up through the opposite side of the wound. The surgeon can then remove the suture cord 18 from the exemplary device 2 and tie a knot therein, which completes the suture.

One of ordinary skill in the art will recognize that additional steps and configurations are possible without departing from the teachings of the invention. This detailed description, and particularly the specific details of the exemplary embodiment disclosed, is given primarily for illustration and no unnecessary limitations are to be understood therefrom, for modifications will become evident to those skilled in the art upon reading this disclosure and may be made without departing from the spirit or scope of the claimed invention.

What is claimed is:

1. A suture cartridge assembly for inserting a stitch through tissue around a hole in an abdominal muscle or a hollow organ, the suture cartridge assembly comprising:
a first arm member holding a first capture sleeve;
a second arm member holding a second capture sleeve; and
a suture cord having a first end attached to the first capture sleeve, a second end attached to the second capture sleeve and an intermediate portion between the first end and the second end, the first arm member and the second arm member being actuated from retracted positions in-line with the suture cartridge assembly to deployed positions for respectively receiving a first penetration member and a second penetration member
a cartridge body comprising a forward end, a connecting end, a first arm receiving cavity for receiving the first arm member on a first side of the cartridge body, a second arm receiving cavity for receiving the second arm member on a second side of the cartridge body, and an arm actuator receiving cavity having an opening at the connecting end;
an arm actuator received within the arm actuator receiving cavity and cooperating with the first arm member, the second arm member, and a center rod member to actuate the first arm member and the second arm member from the retracted positions to the deployed positions and back to the retracted positions; and
a suture spool assembly attached to the forward end of the cartridge body and comprising a spool member for holding the intermediate portion of the suture cord, and a shroud assembly covering the spool member and defining an opening for the first end and the second end of the suture cord to extend respectively from the spool member to the first capture sleeve and the second capture sleeve and for the intermediate portion of the suture cord to unwind from the spool member.

2. The suture cartridge assembly of claim 1, wherein the connecting end of the cartridge body comprises:
a boss for mating with a bore opening of a forward end of a barrel member to provide axial alignment of the suture cartridge assembly and the barrel member; and
an alignment member extending from the connecting end of the cartridge body for mating with a longitudinal alignment slot of the forward end of the barrel member to provide angular alignment of the suture cartridge assembly and the barrel member.

3. The suture cartridge assembly of claim 1, wherein the arm actuator comprises a connecting end, the connecting end being a boss defining a bore hole having a circumferential protrusion therein, the bore hole for receiving a center rod member, the circumferential protrusion serving as a detent to snap fit into a circumferential groove of a forward end of the center rod member for releasable engagement thereof.

4. The suture cartridge assembly of claim 1,
wherein each of the first arm member and the second arm member includes a rotation head end, a capture sleeve end, and an extension portion therebetween, each rotation head end rotatably connected to the cartridge body about a rotation point and having a radial slot radially aligned with the rotation point and a tracking boss protruding from an outboard side thereof, each capture sleeve end releasably holding a respective one of the first capture sleeve and the second capture sleeve; and
wherein the arm actuator comprises:
a first side wall;
a second side wall on an opposite side of the arm actuator from and parallel to the first side wall;
a middle wall between the first side wall and the second side wall and parallel thereto;
a first rod extending between the first side wall and the middle wall at a forward end of the arm actuator;
a second rod extending between the second side wall and the middle wall at the forward end of the arm actuator; and
a J-shaped tracking slot located on an interior surface of each of the first side wall and the second side wall;
wherein the first rod is received in the radial slot of the first arm member and the second rod is received in the radial slot of the second arm member for converting translational motion of the arm actuator into simultaneous rotational motion of the first arm member and the second arm member about each rotation point until each of the first arm member and the second arm member reaches a first attitude at which each tracking boss engages the respective J-shaped tracking slot to maintain the first attitude during further translational motion of the arm actuator.

* * * * *